(12) United States Patent
Bechor et al.

(10) Patent No.: US 8,968,724 B2
(45) Date of Patent: Mar. 3, 2015

(54) COMPOSITIONS SUITABLE FOR TREATMENT OF SPINAL DISEASE, DISORDER OR CONDITION

(75) Inventors: Edna Bechor, Ramat Gan (IL); Liliana Bar, Rehovot (IL); Israel Nur, Moshav Timmorim (IL)

(73) Assignee: Omrix Biopharmaceuticals Ltd., Rehovot (IL)

(*) Notice: Subject to any disclaimer, the term of this patent is extended or adjusted under 35 U.S.C. 154(b) by 1025 days.

(21) Appl. No.: 12/675,234

(22) PCT Filed: Aug. 29, 2008

(86) PCT No.: PCT/IB2008/002259
§ 371 (c)(1),
(2), (4) Date: Aug. 18, 2010

(87) PCT Pub. No.: WO2009/027814
PCT Pub. Date: Mar. 5, 2009

(65) Prior Publication Data
US 2010/0310524 A1    Dec. 9, 2010

Related U.S. Application Data

(60) Provisional application No. 60/935,767, filed on Aug. 30, 2007.

(30) Foreign Application Priority Data

Aug. 30, 2007 (EP) ..................................... 07115352

(51) Int. Cl.
| | | |
|---|---|---|
| A01N 63/00 | (2006.01) | |
| A61L 27/38 | (2006.01) | |
| A61L 27/36 | (2006.01) | |
| C12N 5/077 | (2010.01) | |
| A61K 35/16 | (2006.01) | |

(52) U.S. Cl.
CPC ........... *A61L 27/3856* (2013.01); *A61K 35/545* (2013.01); *A61L 27/3616* (2013.01); *A61L 27/3804* (2013.01); *A61L 27/3878* (2013.01); *C12N 5/0655* (2013.01); *A61K 35/16* (2013.01); *A61L 2430/38* (2013.01); *C12N 2500/84* (2013.01)
USPC ....................................................... 424/93.7

(58) Field of Classification Search
None
See application file for complete search history.

(56) References Cited

U.S. PATENT DOCUMENTS

| | | |
|---|---|---|
| 4,377,572 A | 3/1983 | Schwarz |
| 5,143,838 A | 9/1992 | Kraus et al. |
| 5,792,835 A | 8/1998 | Tse et al. |
| 6,121,232 A | 9/2000 | Nur et al. |
| 6,428,576 B1 | 8/2002 | Haldimann |
| 6,468,527 B2 | 10/2002 | Austin et al. |
| 7,125,569 B2 | 10/2006 | Nur et al. |
| 7,235,255 B2 | 6/2007 | Austin et al. |
| 8,206,448 B2 | 6/2012 | Burkinshaw et al. |
| 8,394,072 B2 * | 3/2013 | Pauza et al. ................... 604/264 |
| 2003/0093362 A1 | 5/2003 | Tupper et al. |
| 2004/0121011 A1 | 6/2004 | McKerracher |
| 2005/0027543 A1 | 2/2005 | Labrou et al. |
| 2005/0148512 A1 | 7/2005 | Hunter et al. |
| 2006/0024229 A1 | 2/2006 | Karp et al. |
| 2006/0224469 A1 | 10/2006 | Kunz et al. |
| 2006/0275273 A1 | 12/2006 | Seyedin et al. |
| 2007/0093905 A1 | 4/2007 | O'Neil et al. |
| 2012/0328600 A1 | 12/2012 | Burkinshaw et al. |

FOREIGN PATENT DOCUMENTS

| | | |
|---|---|---|
| EP | 378798 | 3/1994 |
| EP | 691858 | 12/1999 |
| EP | 534178 | 4/2001 |
| EP | 1390485 | 10/2006 |
| EP | 1894581 | 3/2008 |
| WO | WO 91/00503 | 1/1991 |
| WO | WO 91/14439 | 10/1991 |
| WO | WO 93/05822 | 4/1993 |
| WO | WO 94/23743 | 10/1994 |
| WO | WO 98/33533 | 8/1998 |
| WO | WO 98/55140 | 12/1998 |
| WO | WO 00/47621 | 8/2000 |
| WO | WO 02/095019 | 11/2002 |
| WO | WO 2004/093934 | 11/2004 |
| WO | WO 2006/050267 | 5/2006 |
| WO | WO 2006/050268 | 5/2006 |
| WO | WO 2007/089942 | 8/2007 |
| WO | WO 2007/089948 | 8/2007 |

OTHER PUBLICATIONS

Aota et al 'Differential effects of fibronectin fragment on proteoglycan metabolism by intervertebral disc cells: a comparison with articular chondrocytes' Spine (2005) vol. 30 pp. 722.

Bar, L. et al The binding of fibrin sealant to collagen is influenced by the method of purification and the cross.

Benya, PD et al 'Dedifferentiated chondrocytes reexpress the differentiated collagen phenotype when cultured in agarose gels' Cell (1982) vol. 30 pp. 215.

Cheng, H. et al 'Spinal cord repair in adult paraplegic rats: partial restoration of hind limb funcation' Science (1996) vol. 273 pp. 510-513.

Furtmuller et al 'Tranexamic acid, a widely used antifibrinolytic agent, causes convulsions by a gamma-amniobutyric acid(A) receptor antagonistic effect' J. Pharacol Exp Ther (2002) vol. 301 pp. 168-173.

(Continued)

*Primary Examiner* — Michael Burkhart

(57) ABSTRACT

The invention relates to the use of viral inactivated-plasma cryoprecipitate concentrate (VIPCC) comprising a suitable fibronectin/fibrinogen ratio for treating a spine disease, disorder or condition such as intervertebral disc degeneration.

11 Claims, 8 Drawing Sheets

(56) References Cited

OTHER PUBLICATIONS

Gruber, H.E. et al 'Cell-based tissue engineering for the invtervertebral disc: in vitro studies of human disc cell gene expression and matrix production within selected cell carriers' Spine J (2004) vol. 4 pp. 44-55.

Haudenschild, D.R. et al 'Differential expression of multiple genes during articular chondrocyte redifferentiation' Anat Rec (2001) vol. 263 pp. 91-98.

Hunter et al 'The notochordal cell in the nucleus pulposus: a review in the context of tissue engineering' Tissue Eng (2003) vol. 9 pp. 667-677.

Ju, Y.E. et al 'Enhanced neurite growth from mammalian neurons in three-dimensional salmon fibrin gels' Biomaterials (2007) vol. 28 pp. 2097-2108.

Li, W.J. et al 'Chondrocyte phenotype in engineered fibrous matrix is regulated by fiber size' Tissue Eng (2006) vol. 12 pp. 1775-1785.

Miekka, S.I. et al 'Rapid methods for isolation of human plasma fibrinoectin' Thromb Res (1982) vol. 27 pp. 1-14.

Peretti, G.M. et al 'A biomechanical analysis of an engineered cell-scaffold implant for cartilage repair' Ann Plast Surg (2001) vol. 46 pp. 533-537.

Revell, et al 'Tissue engineered intervertebral disc repair in the pig using injectable polymers' J. Mater Sci Mater Med (2007) vol. 18 pp. 303-308.

Roger, et al 'Evaluating the differences between fibrin sealants: recommendations from an international advisory panel of hospital pharmacists' The European Journal of Hospital Pharmacy Science (2006) vol. 12 Issue 1 pp. 3-9.

Rudert M et al 'Lymph and blood supply of the human intervertebral disc. Cadaver study of correlations to discitis' Acta Orthop Scand (1993) vol. 64 pp. 37-40.

Sachs et al 'Dallas discogram description. A new classification of CT/discography in low-back disorders' Spine (1987) Vo. 12 pp. 287-294.

Walmsley, R 'The development and growth of the intervertbral disc' Edinburgh Med J. (1953) vol. 60 pp. 341-364.

International Search Report re: PCT/US08/02259 dated May 16, 2008.

Jackson, M.R. 'Fibrin sealants in surgical practice: An overview' American Journal of Surgery (2001) vol. 182, No. 2, Supplement pp. 1S-7S.

Perka, C. et al 'The use of fibrin beads for tissue engineering and subsequential transplantation' Tissue Engineering (2001) vol. 7, No. 3 pp. 359-361.

Shirai, T. et al 'Anaphylaxis to aprotinin in fibrin sealant' Internal Medicine (2005) vol. 44, No. 10 pp. 1088-1089.

Szpalski, M. et al 'An overview of blood-sparing techniques used in spine surgery during the perioperative period' European Spine Journal (2004) vol. 13, Suppl. 1 pp. S18-S27.

Tredree, R. et al 'Evaluating the differences between fibrin sealants: recommendations from an international advisory panel of hospital pharmacists' The European Journal of Hospital Pharmacy Science (2006) vol. 12 Issue 1 pp. 3-9.

European Search Report re: EP07115352 dated Feb. 13, 2008.
European Search Report re: EP13157678 dated Apr. 10, 2013.

* cited by examiner

COMPOSITIONS SUITABLE FOR TREATMENT OF SPINAL DISEASE, DISORDER OR CONDITION

CROSS-REFERENCE TO RELATED APPLICATIONS

This application is the national stage of Application No. PCT/IB2008/002259, filed Aug. 29, 2008, which claims priority from U.S. Provisional Application 60/935,767, filed Aug. 30, 2007, and from European Patent Application No. 07115352.2, filed Aug. 30, 2007.

FIELD OF THE INVENTION

The invention relates to the use of a viral inactivated-plasma cryoprecipitate concentrate comprising an initial relative concentration of fibrinogen and fibronectin suitable for treating a spine disease, disorder or condition such as degeneration of a spinal tissue, like intervertebral disc.

BACKGROUND OF THE INVENTION

The intervertebral discs lie between adjacent vertebrae bodies in the spine. Each disc forms a cartilaginous joint that allows slight movements of the vertebrae, acts as a ligament that holds the vertebrae together, and supports compressive loads arising from body weight and muscle tension.

Cartilage is a firm, resilient connective tissue composed of specialized cells called chondrocytes that produce a large amount of extra cellular matrix (ECM). It provides protective cushioning and enables the joints to withstand loads arising from motion needed to perform every-day activities. The body contains three different types of cartilage: articular, which covers joint surfaces; fibro cartilage, which is found in the knee meniscus and intervertebral disc; and elastic cartilage, which is found in the outer ear. The different cartilages are distinguished by their structure, elasticity, and strength.

Aota et al ("Differential effects of fibronectin fragment on proteoglycan metabolism by intervertebral disc cells: a comparison with articular chondrocytes". Spine. 2005; 30:722-728) reported on different effects of fibronectin fragment on proliferation and proteoglycan metabolism in different populations of intervertebral disc and articular chondrocytes. These results suggested that chondrocytes from different cartilage tissue require different conditions for proliferating and for maintaining tissue function.

The intervertebral disc is composed of three basic structures: an inner gel-like substance called the nucleus pulposus (NP), a tough fibrous outer band called the annulus fibrosus (AF), and superior and inferior cartilaginous endplates, which mark the transition between the intervertebral disc and the vertebra. These structures differ in the arrangement of proteoglycan and collagen in the tissue, as well as the relative concentration of each.

During embryonic development three germ layers can be differentiated: the endoderm, the mesoderm, and the ectoderm. These three layers ultimately give rise to internal organs; musculoskeletal tissues; and epidermal and nervous tissues, respectively. A fourth region, known as the notochord, guides the embryonic development of the neural tube; and the vertebral column, including the intervertebral discs. Mesenchymal cells begin to migrate and condense around the notochord to form the osseous vertebral bodies and the annulus fibrosus. The entrapped notochordal cells play a critical role in initiating the development of the nucleus pulposus (Walmsley R. "The development and growth of the intervertebral disc". Edinburgh Med J. 1953; 60:341-364). Thus, these two basic structures of the intervertebral disc, the annulus fibrosus and the nucleus pulposus, are originated from different embryonic origin namely the mesenchyme and the notochord, respectively.

The annulus fibrosus is primarily composed of type I collagen fibrils that form concentric lamellae that surround the nucleus pulposus and insert into the endplates of the adjacent vertebral bodies to form a reinforced structure.

The nucleus pulposus consists of predominantly small chondrocytes-like cells and a second population of large highly vacuolated cells these are the notochordal cells which are presumed remnants of the embryonic tissue that guided formation of the spine and the nuclei pulposi (Hunter et al, "The notochordal cell in the nucleus pulposus: a review in the context of tissue engineering". Tissue Eng. 2003; 9:667-677). Due to the fact that these notochordal cells appear to play a crucial role in formation of the spine and the nucleus pulposus, it is presumed that they could promote repair of the damaged disc and spine. The chondrocytes-like cells express type II collagen, proteoglycan aggrecans, and hyaluronan long chains, which have molecules with highly hydrophilic, branching side chains. These negatively charged regions have a strong avidity for water molecules and hydrate the nucleus or center of the disc by an osmotic swelling pressure. The hydraulic effect of the contained hydrated nucleus within the annulus acts as a shock absorber to cushion the spinal column from forces that are applied to the musculoskeletal system. The vertebral endplates are attached to both the disc and the adjacent vertebral body. The chemical structure of these plates consists of proteoglycan and collagen fibers.

Human intervertebral disc degeneration is a clinical problem, and leading cause of spinal pain and disability. Over 15 million people worldwide suffer from disc degeneration, which is typically characterized by having an altered matrix composition and reduced cell number.

Degenerative Disc Disease (DDD) is an undesired process in which the intervertebral discs lose their flexibility, elasticity, and shock absorbing characteristics. In this process the collagen structure of the annulus fibrosus weakens and becomes brittle. Excessive pressure on a weakened disc can cause tears in the annulus fibrosus, enabling the nucleus pulposus to herniate or extrude through the tears this condition is called herniated disc. The herniated material can compress the nerves around the disc and create pain. A herniated disc can interfere with nerve function, leading to weakness, numbness, inflammation and pain. Additionally, proteoglycan content decreases, thereby reducing the water retaining capabilities of the nucleus pulposus. These changes reduce the ability of the discs to act as shock absorbers and make them less flexible. Loss of fluid also makes the disc smaller and narrows the distance between the vertebrae and the disc.

Since the intervertebral discs are located in a non-vascular environment, the use of tissue engineering of a disc to slow or reverse the degenerative process represents a major biological challenge as they have a limited capacity for repair. Cell activity requires glucose, oxygen, and other nutrients necessary for tissue supporting. However, the disc is the largest avascular tissue in the body. The cells within the disc are sustained by diffusion of nutrients into the disc through the porous central concavity of the vertebral endplate (Rudert M and Tillmann B. "Lymph and blood supply of the human intervertebral disc. Cadaver study of correlations to discitis". Acta Orthop Scand. 1993; 64:37-40).

Degeneration of intervertebral discs or a hematoma can cause spinal cord compression and spinal injury. Spinal cord injury (SCI) usually begins with trauma to the spine that damages the nerves within the spinal canal. Frequent causes of damage are trauma (car accident, gunshot, falls, etc.) or disease (e.g. polio, spina bifida, Friedreich's Ataxia, etc.) and compression of the spine by intervertebral disc herniation. An injury to the spinal cord nerves results in loss or deficit in motor, sensory, and autonomic function. Secondary injury following the primary impact includes a number of biochemical and cellular alterations leading to tissue necrosis and cell death. It is estimated that the annual incidence of SCI is approximately 40 cases per million in the U.S., and that the cost of managing the care of SCI patients approaches $4 billion each year. To date, relatively little progress has been made in the treatment of SCI and related neurological impairments. Currently there is only one accepted, although unapproved, therapy, methylprednisolone. If used in very high doses no later than 8 hours after the injury, methlyprednisolone has demonstrated a modest ability to improve the neurological outcome following SCI.

In the developing vertebrate nervous system, the neural tube is the precursor of the central nervous system (CNS), which comprises the brain and spinal cord. The spinal cord contains communication fibers called axons that transfer sensory and motor information between the brain and the periphery. In transverse section the spinal cord is divided into symmetrical halves by a dorsal median and a ventral median. The dorsal part of the neural tube is primarily associated with sensation, whereas the ventral part is primarily associated with motor (e.g. muscle) control. The term motor neuron classically applies to neurons located in the CNS which project their axons outside the CNS and directly or indirectly control muscles. The term is synonymous with efferent neurons. An injury to the spinal cord has devastating implications resulting in loss of sensation or motor function below the injury level. Following an injury to the CNS, motor neurons are unable to re-grow their axons and they die by necrosis or apoptosis. Published research shows that by transplanting and expressing a second notochord near the dorsal neural tube, 180 degrees opposite of the normal notochord location, one can induce the formation of motor neurons in the dorsal tube, which generally forms sensory cells. An injured CNS is a highly inhibitory environment for axon regeneration, severely limiting functional recovery following injury.

Fibrin glue is typically a blood product obtained from either commercial sources or some regional blood transfusion centers. Components that are commonly used in the preparation of fibrin glue are fibrinogen, thrombin, Factor VIII, Factor XIII, fibronectin, vitronectin and von Willebrand factor (vWF). Fibrin glue formulations are used in surgery, both as a useful addition to sutures and to provide optimal wound integrity, for haemostasis, and for preventing or treating adhesions. Some manufacturers add anti-proteolytic agents to the fibrin glue formulation (as described in WO-A-93/05822) or specifically remove the plasminogen in order to delay or stop the fibrinolysis (as described in U.S. Pat. Nos. 5,792,835 and 7,125,569).

Typically, cryoprecipitation preparation from plasma is the first step in the manufacture of fibrinogen of fibrin based adhesive. Bar et al ("The binding of fibrin sealant to collagen is influenced by the method of purification and the cross-linked fibrinogen-fibronectin (heteronectin) content of the 'fibrinogen' component". Blood Coagul Fibrinolysis. 2005; 16:111-117) reported that fibrin gel formulations prepared from cryoprecipitate differ in their content of fibronectin and heteronectin (fibrinogen-fibronectin covalently linked complexes). The report indicated that content of heteronectin in the formulation influences the fibrin based adhesion to collagen. On the one hand, Schwartz et al (U.S. Pat. No. 4,377, 572) purification procedure results in removal of most of the cross linked fibrinogen-fibronectin molecules, subsequently resulting in a low fibronectin:fibrinogen ratio of 1/14.7 in the formulation and low collagen and gelatin-binding properties of the formed fibrin. On the other hand, the cryoprecipitate preparation described by Martinowitz and Bal (EP-B-691, 858) preserves these cross linked fibrinogen-fibronectin molecules, and consequently has an increased fibronectin/fibrinogen ratio of 1/7 which correlates with increased adherence of the produced fibrin to collagen as compared to adherence to collagen of the fibrin formed with the preparation obtained by the Schwartz purification.

The following publications disclose the use of different fibrin glue preparations in spinal disease. Three-dimensional fibrin matrices as cellular substrates in vitro and as bridging materials for central nervous system repair have been reported. Ju et al ("Enhanced neurite growth from mammalian neurons in three-dimensional salmon fibrin gels. Biomaterials". 2007; 28:2097-2108) reported that salmon fibrin gels were superior scaffold for neuronal re-growth after CNS injury as compared to fibrin prepared from human or bovine blood proteins. Cheng et al ("Spinal cord repair in adult paraplegic rats: partial restoration of hind limb function". Science. 1996; 273:510-513) describes repair of spinal cord gaps in adult rats using peripheral nerve grafts. The grafted area was stabilized with fibrin glue containing acidic fibroblast growth factor.

US patent application US-A-2004/0121011 describes a method for promoting repair, regeneration and re-growth of injured neuronal cells. The application indicated that the nerve injury site can be in the central or in the peripheral nervous system. The formulation combines Rho antagonist and a flowable carrier component capable of forming an acceptable matrix in vivo such as tissue adhesives. US-A-2004/0121011 discloses different protein-based tissue adhesives including collagen gels, fibrin tissue adhesives, matrigel, laminin networks, and adhesives based on a composition of basment membrane proteins that contain collagen. Various commercial preparations are disclosed such as, Tissucol®/TISSEEL®, Beriplast® P, and Hemaseel®.

The following publications disclose the use of fibrin glue compositions in intervertebral disc.

US-A-2005/0148512 relates to injection of a fibrosing agent or a composition comprising a fibrosing agent into damaged intervertebral discs to enhance scarring and support the annular ring of the disc. Fibrinogen-containing formulations such as TISSEAL® are mentioned among numerous compositions which can be delivered into the intervertebral disc.

U.S. Pat. No. 6,428,576 describes a method for repairing defects in the annulus fibrosus using an in-situ curing sealant. The patent discloses a formulation that cure to a viscoelastic material that simulates the structure, physical properties and biomechanical functions of the annulus fibrosus. The cured polymer may be synthetic or naturally occurring. The patent discloses that synthetic polymers are more reliable. The patent discloses several natural occurring proteins, such as albumin, collagen, fibrinogen, fibrin and elastin. These proteins can be from any source such as protein fractionated from blood or recombinant proteins, including processed, denatured or otherwise modified.

WO-A-07/089942 discloses a method of treating a disc, comprising injecting a fibrin sealant into a disc to seal at least one defect of an annulus fibrosus while monitoring the pressure of the fibrin sealant being injected. The fibrin sealant comprises fibrinogen and an activating compound such as thrombin. According to the description the defect can be a tear or a fissure in the annulus fibrosus or a fibrous capsule of a spinal joint. The description discloses use of any fibrinogen that will form fibrin in a human body. Fibronectin is mentioned as one of numerous possible additives to the fibrinogen composition.

WO-A-06/050268 discloses an injection of fibrin sealant into a tear or a fissure in the annulus fibrosus. The sealant comprises fibrinogen and activating compound such as thrombin. According to the application, the fibrinogen component can be autologous, human including pooled human fibrinogen, recombinant, and bovine or other non-human source. Fibronectin is mentioned among many components as an additional additive which can be employed in the fibrin sealant.

Also WO-A-06/050267 discloses the injection of fibrin sealant and anesthetic into the spinal area to seal defects in the annulus fibrosus, such as tears or fissures. According to the description, the fibrinogen component includes any fibrinogen that will form fibrin in human body. The application mentions commercial kits from manufacturers as Baxter such as TISSEEL®. The description of WO-A-06/050267 discloses that alternative amounts of fibrinogen may be used in order to change the density of the combined components.

WO-A-07/089948 relates to a method of treating a disc that is leaking nucleus pulposus into and/or thorough at least one defect in the annulus fibrosus. The method comprises injecting a biological sealant, such as fibrinogen solution and activating solution to the spinal area using a multi-lumen catheter. The description also relates to a kit comprising a biological sealant and a biological sealant apparatus for injecting fibrin sealant into a human disc.

U.S. Pat. No. 6,468,527 describes a two component fibrin sealant including a biological or non-biological agent. The composition provides a mean for delivering a particular agent to a specific critical site within the body and providing a prolonged, time release therapeutic value. Injections of fibrin glue infused with corticosteroids into the lumbar epidural space and into the intra discal space are specifically disclosed. The fibrin sealant acts to maintain extended anti-inflammatory response of the corticosteroid and to seal the annular fissures, which otherwise allow damaging chemicals to escape from the disc space and bathe the nerve root resulting in chemical radiculitis. Also, U.S. Pat. No. 7,235,255 discloses a system for delivering a biological tissue adhesive comprising a fibrinogen component, a thrombin component, and a corticosteroid-containing solution. According to the description the fibrin sealant can be used to treat degenerative disc and incompetent disc disease. Exemplified is an intradiscal injection. The delivery system seals, protects the exposed nerve roots from further chemical damage, and acts as a vehicle to maintain corticosteroids in a lasting deposition on the nerve root.

The following publications report tissue engineering as a possible biologic approach, which aims to replace, repair, maintain, and/or enhance tissue function by combination of cells, suitable biochemical and physiochemical factors and optionally a porous structure to be employed as scaffold. WO-A-04/093934 discloses a method of augmenting and/or repairing an intervertebral disc by administering stem cell material into the disc. The stem cell material is provided in a biologically compatible lattice material. The preferred lattice material is lipo-derived lattice such as proteoglycans, glycoproteins, hyaluronins, fibronectins, collagens (type I, type II, type III, type IV, type V, type VI, etc.), and the like. According to the description of WO-A-04/093934 the lipo-derived lattices serve as excellent substrates for cell growth. Exemplified are only collagen-based lattice materials.

WO-A-00/47621 discloses a method for producing a viral inactivated cryoprecipitate having a preferred fibrinogen and fibronectin ratio of from 0.02 to 0.5 which e.g. can be used to produce a fibrin based biomatrix suitable for growing any human cells and keratinocytes, fibroblasts and chondrocytes are mentioned. In one preferred embodiment, the antifibrinolytic agent t-AMCHA (i.e. tranexamic acid) which is indicated to advantageously lower the viscosity of the composition is used.

U.S. patent application Ser. No.06/0275273, describes a method for implantation or injection of chondrocytes into a degenerative intervertebral disc. The patent discloses chondrocytes obtained from cadaver. According to the description the chondrocytes can be obtained from cartilage tissue, including intervertebral disc cartilage, or cartilage originating from cartilaginous tissues other than intervertebral disc tissue. The description discloses several biocompatible molecules to be added to the cell composition such as laminin, chitosan, hydrogel, pegylated hydrogel, collagen type I, II, III, fibrinogen, fibrin, thrombin, fibronectin and hyaluronic acid. Disclosed is the use of commercial formulation TISSEEL® fibrin glue with the cells. The examples also disclose the use of cryoprecipitated porcine fibrinogen and a chondrocyte-thrombin solution.

U.S. patent application Ser. No.07/0093905 discloses a mixture for repair and regeneration of intervertebral discs comprising glycine, concentrated monocytes and fibrin glue. The patent also discloses excised and treated nucleus or annular tissue for reinsertion into the disc. The reinserted disc cells can optionally be combined with carriers such as a gel-like carrier or an adhesive. The gel like carrier can be a biological or synthetic hydrogel, hyaluronic acid, collagen gel, mussel-based adhesive, fibrin glue, fibrin clot, blood, blood clot, blood component, blood component clot etc. The patent application does not mention a specific composition of the disclosed carriers, and is silent on a cryoprecipitate concentrate.

EP-A-1,894,581 discloses a matrix gel comprising chondrocytes or progenitor cells as a cartilage repair implant. According to the description the gel matrix provides a simple dilution of primary chondrocytes resulting in increased production of extra cellular matrix material. In a preferred embodiment the chondrocytes are isolated from articular cartilage. Fibrin glue is mentioned among numerous matrix gel material that can be used. The application does not mention a specific composition of the matrix gel material and is silent on a particular relative concentration among the gel components.

Disc cells grown in monolayer assume a fibroblast-like phenotype. In a three-dimensional environment, however, disc cells become rounded, form colonies, and exhibit greater proliferation and proteoglycan synthesis. Various in vitro culture techniques, including complex three-dimensional gels and degradable polymer scaffolds have been developed with the goal of providing a sustainable frame on which the disc cells can proliferate. Hyaluronic acid, collagen, chitosan and fibrin gel have been used in cross-linkable polymeric preparation to entrap cells.

In spite of all the techniques reported on the use of fibrin glue in IVD, Gruber et al ("Cell-based tissue engineering for the intervertebral disc: in vitro studies of human disc cell gene expression and matrix production within selected cell carriers". Spine J. 2004; 4:44-55) reported that fibrin gel formulations were inferior microenvironments for proliferation, ECM production and gene expression of annulus fibrosus cells. The term "extra cellular matrix", abbreviated "ECM", refers to the complex structural material that is produced by cells in mammalian tissues. The extra cellular matrix is typically the defining feature of a connective tissue, for example, chondrocyte cells. The ECM in vivo usually provides structural support to the cells.

There is a need for an optimal fibrin composition suitable for treating a spine disease, disorder or condition such as intervertebral disc degeneration.

SUMMARY OF THE INVENTION

Fibrin glues are well known and are used extensively in various clinical setting. Such glues are used in surgery, both as a useful addition to sutures and to provide optimal wound integrity, for haemostasis, and for preventing or treating adhesions. Recently, literature on the use of fibrin glue to reconstruct spinal intervertebral disc, sealing fissures in the annulus fibrosus and in central nervous system restoration has been published.

It was found according to the present invention that an increase in fibrinogen concentration in coated plates significantly decreased the attachment of the intervertebral disc nucleus pulposus cells to the plates whereas an increase in the ratio fibronectin/fibrinogen concentration lead to the opposite outcome. On the other hand a fibrin glue composition such as cryoprecipitate which is selectively depleted of fibrinogen and comprises high levels of fibronectin would not cure and therefore will not form a supporting three-dimensional scaffold for the cells. The present invention solves this technical problem and provides cryoprecipitate with optimal fibronectin and fibrinogen concentrations for use in intervertebral disc.

It was found according to the present invention that fibronectin/fibrinogen ratio plays a crucial role in the nucleus pulposus cell attachment, proliferation and migration and absolutely depends on a high content of fibronectin relative to fibrinogen. For example, it was found according to the invention that nucleus pulposus cells cultured in a mixture which comprises an increased fibronectin/fibrinogen ratio of about 1/10-1/5 show increased cell-attachment and proliferation as compared to the cells cultured in a mixture which comprises a lower fibronectin/fibrinogen ratio. Also, it was shown herein that a cryoprecipitate with the increased fibronectin/fibrinogen ratio was able to restore disc height when injected into the nucleus pulposus area. Thus, a cryoprecipitate comprising a fibronectin/fibrinogen ratio higher than 1/12 and in the range of 1/10-1/5, such as 1/7 can be used as a superior component of a matrix for restoring disc height while serving as an optimal scaffold for nucleus pulposus cells.

Studies indicate that notochord cells can guide the formation of nucleus pulposus and CNS cells and/or can be used as progenitors of such cells. Therefore, the cryoprecipitate according to the invention can be used to assist in reconstruction of the intervertebral disc and the central nervous system (CNS).

Tranexamic acid is a synthetic fibrinolysis inhibitor, which has been shown to affect the central nerve system (CNS) causing hyper-excitability and convulsions probably as a result of it being an antagonist of Gamm-Aminobutyric Acid (GABA) (Furtmüller et al. "Tranexamic acid, a widely used antifibrinolytic agent, causes convulsions by a gamma-aminobutyric acid(A) receptor antagonistic effect". J Pharmacol Exp Ther. 2002; 301:168-173; Roger et al. "Evaluating the differences between fibrin sealants: recommendations from an international advisory panel of hospital pharmacists". The European Journal of Hospital Pharmacy Science Volume 12, 2006, Issue 1, P. 3-9).

Also, it has been shown that bovine aprotinin is a highly immunogenic serine protease inhibitor which can cause a very rare and incurable degenerative neurological disorder called Creutzfeldt-Jakob disease (CJD), which causes a spongy degeneration in the brain and the spinal cord. Thus, according to the method of the invention, substances as tranexamic acid and bovine aprotinin are excluded from the cryoprecipitate concentrate of the invention to be used at the spine.

Therefore, the disclosed art neither discloses nor suggests the optimal fibrin glue for use in the spine prepared with a cryoprecipitate formulation having a suitable fibrinogen and fibronectin ratio and lacking tranexamic acid and/or-bovine derived aprotinin.

In one aspect, the invention refers to the use of viral inactivated-plasma cryoprecipitate concentrate (VIPCC), optionally in combination with a cell composition comprising notochordal-derived cells, wherein the cryoprecipitate comprises an initial fibronectin/fibrinogen relative concentration of higher than 1/12 or about 1/11 to about 1/5 for treating a spine disease, disorder or condition with the proviso that tranexamic acid and bovine aprotinin are absent from the cryoprecipitate concentrate.

In one embodiment of the present invention, the VIPCC comprises a fibronectin/fibrinogen ratio of about 1/10 to about 1/5.

In another embodiment of the present invention, the VIPCC is activated.

In another embodiment of the present invention, the VIPCC comprises a contrast agent. The contrast agent can be iodine.

In another further embodiment of the present invention, the VIPCC is used for treating an intervertebral disc disease, disorder or condition.

In one embodiment of the invention, the VIPCC is used for restoring, at least partially, the intervertebral disc height of a damaged IVD.

Yet in another embodiment of the invention, the VIPCC is used for preventing intervertebral disc herniation.

Yet in another further embodiment of the invention, the disease is an early stage of intervertebral degenerative disease.

Still in another embodiment of the invention, the activated VIPCC serves as a scaffold for reconstruction of nucleus pulposus cells at advanced stage of intervertebral degenerative disc disease.

In still another further embodiment of the invention, the activated VIPCC serves as a scaffold for reconstruction of injured or ruptured spinal cord.

In another aspect, the invention relates to the use of a kit comprising a first container comprising viral inactivated-plasma cryoprecipitate concentrate (VIPCC) having a fibronectin/fibrinogen ratio of higher than 1/12, or about 1/11 to about 1/5, and a second container comprising an enzyme capable of forming fibrin when it reacts with fibrinogen for treating a spine disease, disorder or condition, with the proviso that tranexamic acid and bovine aprotinin are absent from the kit.

In one embodiment of the invention, said VIPCC comprises a fibronectin/fibrinogen ratio of about 1/10 to about 1/5.

In another embodiment of the invention, the kit is used for treating an intervertebral disc disease, disorder or condition. The kit can further comprise a contrast agent such as iodine.

Still in another aspect the invention relates to the use of a scaffold comprising viral inactivated-plasma cryoprecipitate concentrate (VIPCC) having an initial fibronectin/fibrinogen relative concentration of higher than 1/12, or about 1/11 to about 1/5 for treating a spine disease, disorder or condition, with the proviso that tranexamic acid and bovine aprotinin are absent from the cryoprecipitate concentrate and sacffold.

In one embodiment of the invention, said VIPCC comprises a fibronectin/fibrinogen ratio of about 1/10 to about 1/5.

In another embodiment of the invention, the scaffold is used for treating an intervertebral disc disease, disorder or condition.

Yet in another aspect the invention relates to a kit comprising: a first container comprising a viral inactivated-plasma cryoprecipitate concentrate (VIPCC) having a fibronectin/fibrinogen ratio of higher than 1/12 or about 1/11 to about 1/5, a second container comprising an enzyme capable of forming fibrin when it reacts with fibrinogen, and a third container comprising a proteolytic enzyme selected from the group consisting of serine peptidases, cystein peptidases, aspartic peptidases, metallo peptidases, hyaluronidase and combinations thereof.

Still in another embodiment of the invention, the proteolytic enzyme is selected from the group consisting of trypsin, chymotrypsin, pancreatic elastase, papain chymopapain, pepsin, collagenase, gelatinase, pronase chondroitinase, hyaluronidase and combinations thereof The kit can further comprise a contrast agent such as iodine.

Another object of the invention is to provide a vehicle suitable for delivering a composition of cells into a damaged spine tissue comprising viral inactivated-plasma cryoprecipitate concentrate (VIPCC) having an initial fibronectin/fibrinogen relative concentration higher than 1/12 or about 1/11 to about 1/5 and notochordal derived cells, with the proviso that tranexamic acid and bovine aprotinin are absent from the cryoprecipitate concentrate.

In one embodiment of the invention, the VIPCC has an initial fibronectin/fibrinogen relative concentration of about 1/10 to about 1/5.

In another embodiment of the invention, the damaged spine tissue is intervertebral disc.

In another further embodiment of the invention, the notochordal-derived cells are nucleus pulposus cells.

Another aspect of the invention relates to a tissue or cell bank comprising notochordal-derived cells in a composition comprising viral inactivated-plasma cryoprecipitate concentrate (VIPCC) having an initial fibronectin/fibrinogen relative concentration of higher than 1/12 or about 1/11 to about 1/5.

In one embodiment of the invention, said VIPCC comprises a fibronectin/fibrinogen ratio of about 1/10 to about 1/5.

In another embodiment of the invention, said cells are nucleus pulposus cells.

Yet another object of the invention relates to the use of viral inactivated-plasma activated cryoprecipitate concentrate, wherein said cryoprecipitate comprises an initial fibronectin/fibrinogen relative concentration of higher than 1/12 or about 1/11 to about 1/5 for treating a spine disease, disorder or condition, with the proviso that bovine aprotinin is absent from the cryoprecipitate concentrate.

The cryoprecipitate can comprise an initial fibronectin/fibrinogen relative concentration of about 1/10 to about 1/5.

In one embodiment of the invention, said cryoprecipitate is used for treating an intervertebral disc disease, disorder or condition.

The kit, cells from the tissue or cell bank and/or the vehicle obtainable according to the invention can be used for treating a spine disease, disorder or condition such as degeneration of a spinal tissue, like intervertebral disc.

In another aspect of the invention, the viral inactivated-plasma activated cryoprecipitate concentrate is used for increasing or restoring at least partially the intervertebral disc height. The cryoprecipitate comprises an initial fibronectin/fibrinogen relative concentration of about 1/11 to about 1/5 and tranexamic acid and bovine aprotinin are absent from the cryoprecipitate concentrate.

In one embodiment of the invention, said cryoprecipitate comprises an initial fibronectin/fibrinogen relative concentration of about 1/10 to about 1/5.

Yet in another aspect the invention relates to a method for facilitating growth, proliferation, differentiation, maintenance, repair and/or restoration of notochordal-derived cells comprising contacting the population of said cells with viral inactivated-plasma cryoprecipitate concentrate (VIPCC) having an initial fibronectin/fibrinogen relative concentration of higher than 1/12 or about 1/11 to about 1/5, with the proviso that tranexamic acid and bovine aprotinin are absent from the cryoprecipitate concentrate.

In one embodiment of the invention, said VIPCC comprises a fibronectin/fibrinogen ratio of about 1/10 to about 1/5.

In another embodiment of the invention, said cells are nucleus pulposus cells. In another embodiment of the invention, the VIPCC is activated.

In another further embodiment of the invention, said contacting is carried out ex vivo. Yet in another further embodiment of the invention, said contacting is carried out in vivo.

One object of the present invention is to provide a method for treating a spine disease, disorder or condition such as degeneration of a spinal tissue, like intervertebral disc comprising administering into the spine of a subject in need a viral inactivated-plasma cryoprecipitate concentrate (VIPCC), optionally in combination with a cell composition comprising notochordal-derived cells, wherein the cryoprecipitate comprises an initial fibronectin/fibrinogen relative concentration of higher than 1/12 or about 1/11 to about 1/5, with the proviso that tranexamic acid and bovine aprotinin are absent from the cryoprecipitate concentrate.

In one embodiment of the invention, the VIPCC is activated.

In another embodiment of the invention, the VIPCC is administered in combination with a cell composition comprising notochordal-derived cells. In another further embodiment of the invention, said cells are nucleus pulposus cells.

Yet in another embodiment of the invention, all or a portion of the nucleus pulposus tissue is excised prior to administering the VIPCC and the cells.

Still in another embodiment of the invention, prior to the administering of the cells, they are cultured ex-vivo on VIPCC comprising a fibronectin/fibrinogen ratio of about 1/11 to about 1/5.

Another object of the present invention is to provide a method for treating a spine disease, disorder or condition such as degeneration of a spinal tissue, like intervertebral disc comprising administering to a subject in need a kit, cells from a tissue or cell bank and/or a vehicle according to the invention.

BRIEF DESCRIPTION OF THE DRAWINGS

The features, aspects, and advantages of the present invention will become better understood with regard to the following description, examples, claims, and the following figures.

DETAILED DESCRIPTION OF THE INVENTION

Figure 1:
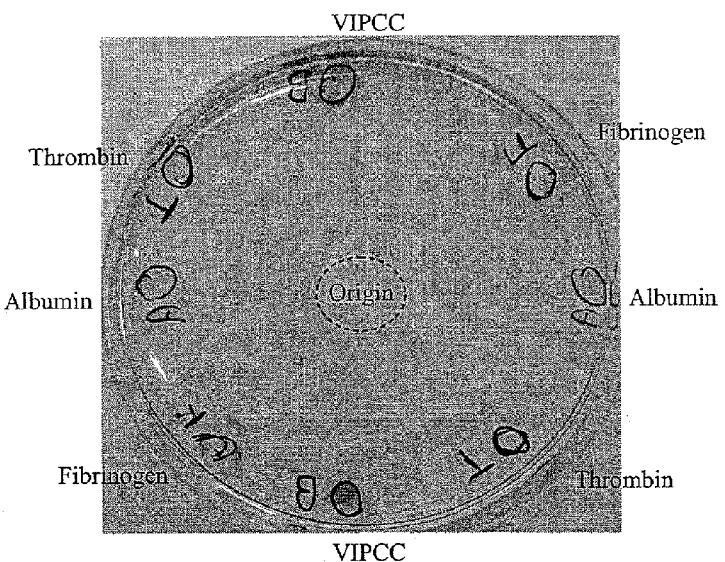
FIG. 1: shows the effect of thrombin, viral inactivated-plasma cryoprecipitate concentrate (VIPCC) and components thereof on attachment and proliferation of annulus fibrosus cells. A 97-mm plastic culture dish was coated at the circumference with VIPCC, thrombin, albumin and fibrinogen. Afterwards, annulus fibrosus cell suspension was seeded in the center of the dish (Origin). Cell attachment to VIPCC, thrombin, albumin and fibrinogen was determined after 14 days by Hematoxylin and Eosin staining.

The invention relates to the use of viral inactivated-plasma cryoprecipitate concentrate (VIPCC) comprising a suitable fibronectin/fibrinogen ratio for treating a spine disease, disorder or condition such as intervertebral disc (IVD) degeneration.

It was surprisingly found according to the present invention that fibronectin/fibrinogen ratio plays a crucial role in nucleus pulposus cell attachment, proliferation and migration.

It has been shown according to the invention that conductivity properties of cryoprecipitate on the nucleus pulposus (NP) absolutely depend on an optimal ratio of fibronectin relative to fibrinogen.

The term "cryoprecipitate" refers to a blood component which is obtained from frozen plasma prepared from whole blood. A cryoprecipitate can be obtained when frozen plasma is thawed in the cold, typically at a temperature of 0-4° C., and collecting the precipitate, for example by centrifugation. Usually a cryoprecipitate is formed which is rich in fibrinogen, factor VIII, von Willebrand factor, factor XIII, and fibronectin. The cryoprecipitate component can be prepared from autologous plasma, human including pooled plasma, or of non-human source plasma.

The results obtained according to the invention show that an increase in fibrinogen concentration in coated plates significantly decreased nucleus pulposus cell attachment to the plates. While an increase in fibronectin concentration in the plates caused the opposite outcome. However, cryoprecipitate which is selectively depleted of fibrinogen and composes high levels of fibronectin would not cure, and therefore without fibrinogen a scaffold which supports a three-dimensional tissue formation will not form.

More specifically, it was found according to the invention that a purified mixture of fibronectin/fibrinogen in a ratio of 1/10 and 1/5 is more suitable for attachment and proliferation of nucleus pulposus cells than mixtures comprising a lower fibronectin/fibrinogen ratio. Surprisingly, in contrast to annulus fibrosus, nucleus pulposus cell attachment was found to be affected by an increase in fibrinogen concentration in fibrinogen coated plates. In fact, attachment of nucleus pulposus cells significantly decreased with increased fibrinogen concentrations in a dose-depended manner. In contrast, increase in fibronectin/fibrinogen ratio lead to the opposite outcome. These results indicate the key role of fibronectin/fibrinogen ratio in nucleus pulposus cell attachment and demonstrate the advantage of using a high level ratio of fibronectin/fibrinogen for nucleus pulposus cells. The results obtained indicate that nucleus pulposus cell attachment is better on VIPCC than in a purified mixture of fibronectin/fibrinogen having a high and similar ratio of fibronectin/fibrinogen. Of note, cell attachment of annulus fibrosus chondrocytes was similar on both coatings.

Cell proliferation of nucleus pulposus and annulus fibrosus cells was higher on the VIPCC coating than on the coating composed of purified fibronectin and fibrinogen mixture. However, proliferation of nucleus pulposus chondrocytes was more affected than that of annulus fibrosus condrocytes by the different coatings. Viability of nucleus pulposus cells on a VIPCC coating with high fibronectin/fibrinogen ratio and a purified fibronectin/fibrinogen mixture was also monitored. The results show that high fibronectin/fibrinogen ratio was able to mitigate the decrease in cell viability observed in the fibrinogen alone coating. This positive effect on nucleus pulposus cells was particularly pronounced with the VIPCC coating. These results show the advantages of using the VIPCC with high fibronectin/fibrinogen ratio as a coating for nucleus pulposus cells instead of the pure fibronectin/fibrinogen mixture. It was found that nucleus pulposus chondrocytes sense a chemotactic gradient of various VIPCC dilutions and transmigration occurred in the presence of such VIPCC gradient. Thus, a VIPCC formulation with high fibronectin/fibrinogen ratio can have chondro-conductive characteristics.

In all, the results according to the invention show that VIPCC according to the invention, having a fibronectin/fibrinogen ratio higher than 1/12, or from about 1/11 to about 1/5, or from about 1/10 to about 1/5, from about 1/10 to about 1/7 or of about 1/7 is suitable for use with nucleus pulposus cells. Thus, activated VIPCC of the invention can be used as a scaffold for growing nucleus pulposus cells ex-vivo or can be injected into the intervertebral disc space to be used as a scaffold for nucleus pulposus cells in vivo.

It was found according to the invention that injection of VIPCC and thrombin into the intervertebral disc of an animal model did not change the structure of IVD and that the typical structure of chondrocyte tissue in the IVD was preserved. Also, it was shown that activated-VIPCC can function to substantially restore normal disc height and such restored disc is able to resist compressive loads like natural nucleus pulposus tissue.

In addition, maintenance of morphology and functionality of IVD injected nucleus pulposus chondrocytes was demonstrated when injected together with activated-VIPCC according to the invention.

Thus a viral-inactivated plasma cryoprecipitate concentrated (VIPCC) having a fibronectin/fibrinogen ratio higher than 1/12, or from about 1/11 to about 1/5, or from about 1/10 to about 1/5 from about 1/10 to about 1/7 or of about 1/7 can be advantageously used to allow attachment, proliferation and migration of cells from nucleus pulposus tissue. The results also show that nucleus pulposus cells cultured in activated VIPCC according to the present invention maintain morphology and synthesis of chondroitin sulfate. Since nucleus pulposus cells originate from and/or are guided by the notochord region, these results pave the way to new approaches for therapy of injured spine whose formation is guided by notochordal cells such as nucleus pulposus and motor neurons from central nervous system. Therefore cryoprecipitates containing optimal ratio of fibronectin/fibrinogen are superior over a cryoprecipitate not containing fibronectin or comprising a low ratio of fibronectin/fibrinogen for use in the spine.

The cells of human nucleus pulposus tissue of the IVD are primarily small chondrocyte-like cells, but there is a second population of large cells, the notochordal cells, which are presumed remnants of the embryonic tissue that guided formation of the embryonic development of the neural tube and the nucleus pulposus (Hunter et al, 2003). Some studies indicate that notochord cells found in the nucleus pulposus tissue can guide the formation of nucleus pulposus and CNS cells. Therefore, nucleus pulposus tissue can be used to assist in reconstruction of the intervertebral disc and the CNS.

In one aspect, the invention relates to a method for facilitating growth, proliferation, differentiation, maintenance, repair and/or restoration of notochordal derived cells such as nucleus pulposus cells, the method of which comprises contacting the population of said cells with viral inactivated-plasma cryoprecipitate concentrate (VIPCC) having an initial fibronectin/fibrinogen relative concentration of higher than 1/12 or from about 1/11 to about 1/5, or from about 1/10 to about 1/7 or of about 1/7. In one embodiment of the invention, the initial fibronectin/fibrinogen relative concentration is from about 1/10 to about 1/5.

The term "notochord derived cells" refers to cells which formation was guided by the notochord region. In other words, notochord derived cells refer to spinal nucleus pulposus cells and spinal neural cells (namely CNS cells).

Tranexamic acid is a synthetic fibrinolysis inhibitor, which has been shown to affect the central nerve system (CNS) causing hyper-excitability and convulsions probably as a result of it being an antagonist of Gamm-Aminobutyric Acid (GABA) (Furtmüller et al. "Tranexamic acid, a widely used antifibrinolytic agent, causes convulsions by a gamma-aminobutyric acid(A) receptor antagonistic effect". J Pharmacol Exp Ther. 2002; 301:168-173; Roger et al. "Evaluating the differences between fibrin sealants: recommendations from an international advisory panel of hospital pharmacists". The European Journal of Hospital Pharmacy Science Volume 12, 2006, Issue 1, P. 3-9).

Also, it has been shown that bovine aprotinin is a highly immunogenic serine protease inhibitor which can cause a very rare and incurable degenerative neurological disorder called Creutzfeldt-Jakob disease (CJD), which causes a spongy degeneration in the brain and the spinal cord.

Thus, according to the method of the invention, substances as tranexamic acid and/or bovine aprotinin are excluded from the cryoprecipitate concentrate to be used at the spine. VIPCC in which the levels of plasminogen and plasmin were lowered makes the use of these substances unnecessary. In one embodiment of the invention, in the VIPCC plasminogen and plasmin have been lowered to equal or less than 15 μg/ml like for example 5 μg/ml.

The plasma cryoprecipitate according to the present invention can be activated or non-activated. The term "activated VIPCC" refers to the cryoprecipitate composition after combination with an activating component which is capable to form fibrin from fibrinogen. The combined mixture results in a three-dimensional structure. The activating component can be thrombin and/or a solution obtainable from snake venom. The contacting of VIPCC of the invention with the cells can be carried ex-vivo, including in vitro cell culturing with or without other cell types or in vivo at the injured site.

The disclosed art neither suggests nor discloses the use of a cryoprecipitate formulation having a preferred fibrinogen and fibronectin ratio, lacking tranexamic acid and bovine derived aprotinin for use in the spine.

In one aspect, the invention relates to a method for treating and/or preventing a spine disease, disorder or condition such as intervertebral disc degeneration comprising administering into the spine of a subject in need a viral-inactivated plasma cryoprecipitate concentrated (VIPCC) having an initial fibronectin/fibrinogen ratio higher than 1/12, from about 1/11 to about 1/5, with the proviso that tranexamic acid and bovine aprotinin are absent from the cryoprecipitate concentrate. The VIPCC composition according to the invention can be administered in combination with a cell composition comprising notochord derived cells such as nucleus pulposus cells.

In one embodiment of the invention, the VIPCC comprises an initial fibronectin/fibrinogen relative concentration of from about 1/10 to about 1/5. According to the present invention, said VIPCC can be activated or non-activated.

As used herein, the term "initial" refers to the variables ratio at the end of the cryoprecipitate concentrate preparation.

In another aspect, the invention provides a method useful for treating central nervous system (CNS) disease, disorder or condition comprising administering to the site of the injury or damage of a subject in need a viral-inactivated plasma concentrated cryoprecipitate (VIPCC) having a fibronectin/fibrinogen ratio higher than 1/12, from about 1/11 to about 1/5. In another embodiment, the invention is useful for treating injury of the CNS or the spinal cord, and enhances CNS restoration and axonal growth in a subject.

The term "spine disease, disorder or condition" refers to intervertebral disc and/or to central nervous system disease, disorder or condition.

The term "intervertebral disc disease, disorder or condition" refers to multiple disorder, disease or conditions involving intervertebral disc degeneration and/or injury such as disc herniation, fissured disc, spinal stenosis, black disc, disc pain, etc.

Oftentimes, the term "intervertebral disc disease, disorder or condition" is used as synonymous with the term "Degenerative Disc Disease (DDD)".

In accordance with the "modified Dallas Discogram" naming system there are six possible categories that describe the severity of the radial annular tear (grade 0-5) (Sachs et al. "Dallas discogram description. A new classification of CT/discography in low-back disorders". Spine. 1987; 12:287-294). While the grade 0 describes a normal disc; where no contract material leaks from the nucleus and the grade 5 tear describes a tear that has completely ruptured the outer layers of the disc and is leaking material out of the disc.

Inadequate disc nutrition e.g. when the blood supply from the adjacent vertebrae is impaired, disc degeneration may be accelerated. This may be caused by nucleus pulposus dehydration leading to degradation of the collagenous fibers. Such dehydrated discs can be seen on an MRI scan and are also known as 'black discs' because of the colour change on MRI. Ultimately, the disc may lose its shock absorbing ability. The disc space will become narrow, lose its shock absorbing ability and movement at that level will be abnormal. This places excessive strain on adjacent structures in the spine leading to nerve root compression, a painful condition called spinal stenosis (http://www.saspine.org/conditions/ddd_disease-.htm).

Diagnostic tests for a spinal disease, disorder or condition include, but are not limited to, roentgenography, myelography, computed tomography, magnetic resonance imaging, positron emission tomography, and other diagnostic tests known in the art.

As used herein the term "central nervous system disease, disorder or condition" refers to any disease, disorder, or trauma that disrupts the normal function or communication of the brain or spinal cord. The CNS injuries which can be treated according to the present invention are diverse and will be easily understood by the skilled person. Without limitation, there may be mentioned brain and spinal cord injuries due to neurosurgery, trauma, ischemia, hypoxia, neurodegenerative disease, metabolic disorder, infectious disease, compression of the inervertebral disc, tumors and autoimmune disease.

The administration of the VIPCC composition to the intervertebral disc can be carried out by injection. In such an embodiment, the injection procedure can be carried as follows. The subject in need can be positioned laterally and bended forward. The needle or cannula can be inserted into the nucleus pulposus of the disc to be treated. When treating a central nervous system defect, the needle or cannula can be positioned adjacent to the dura. The needle or cannula can be inserted under the guidance of a tracer. The term "tracer" is interchangeable with the term "contract agent" as defined below. The technique which may be used in the method of the invention includes fluorography, scanning, magnetic resonance imaging, tomography, nanotechnology, digital video, X-ray or any other technique known in the art. Non limiting examples of tracers are organic dyes, food dyes and/or fluorescent dyes. The contrast agent may be chosen from various non-toxic agents, such as iodine. If the spectrum of the tracer is not visible to the human eye the tracer can be detected by appropriate equipment. Once in proper position, the needle or cannula can be inserted into the nucleus pulposus e.g. after traversing the annulus fibrosus. Then the contrasting agent is injected in order to verify the exact application site. The contrast agent can be present at the end of the tip of the needle or cannula. Once the location is verified the VIPCC and e.g. an equal volume of an activating component are injected into the intradiscal space. The injection procedure can be in any order, for example, the components are applied simultaneously or one after the other and a scaffold is formed when the components are mixed.

The term "activating component" refers to a compound that is capable to form fibrin from fibrinogen including thrombin and/or a solution obtainable from snake venom. In an embodiment of the invention, the thrombin is isolated from plasma of human beings or mammals. It is also possible that the enzyme which is capable to form fibrin is prepared by recombinant methods.

The activated VIPCC can be injected in combination with a cell composition comprising notochordal derived cells such as nucleus pulposus cells.

The activated VIPCC can be used in an amount suitable for the reconstruction of the damaged area and is dependent on the extent of the injury.

The components can be injected at the base of the defect and the needle or cannula can be withdrawn from the annulus fibrosus when encountered resistance. Excess solutions can be spilt out of the injection site, forming a solid gel and a closure of the aperture or incision following the injection.

In one embodiment of the invention, the VIPCC comprises a fibronectin/fibrinogen ratio of about 1/7. The term "viral-inactivated plasma concentrated cryoprecipitate" relates to a cryoprecipitate of whole blood having a fibronectin/fibrinogen ratio higher than 1/12, for example as described in EP-B-534,178 and WO-A-9305822, and obtainable by thawing a cryopaste;
dissolving in a buffer at pH 7.0 to 7.2;
preheating to 30 to 35° C.;
adjusting pH to 7.0 to 7.2;
adding aluminum hydroxide under stirring;
centrifuging and discarding the precipitate;
adding $CaCl_2$;
virus inactivation;
concentrating by ultrafiltration to a protein concentration of 60 to 100 mg/ml.

Currently, fibrin glue or fibrin formulations have been disclosed for use in intervertebral disc and central nervous system regeneration, however, we found according to the present invention that cryoprecipitate, such as the one prepared according to the Martinowitz and Bal method, which contains a high fibronectin/fibrinogen ratio, close to the ratio of the original cryoprecipitate and wherein the cryoprecipitate composition does not include tranexamic acid and/or bovine aprotinin is more suitable for enhancing adhesion, proliferation, growth, differentiation, and/or maintenance of cells in nucleus pulposus tissue than compositions comprising a lower fibronectin/fibrinogen ratio and contain tranexamic acid and/or bovine aprotinin. The disclosed art neither suggests nor discloses the use of a cryoprecipitate formulation having a preferred fibrinogen and fibronectin ratio, lacking tranexamic acid and bovine derived aprotinin for use in abnormal nucleus pulposus.

Other commercial formulations such as TISSEEL®, Tissucol® have a lower fibronectin/fibrinogen ratio than the original cryoprecipitate and contain tranexamic acid and/or bovine aprotinin, thus the cryoprecipitate of the invention comprising a ratio of more than 1/12, from about 1/11 to about 1/5, from about 1/10 to about 1/5, from about 1/10 to about 1/7 and of about 1/7, for example BAC; Omrix, I L prepared as described in EP-B-534,178, wherein the plasmin and plasminogen are removed as described in EP-B-1,390, 485 and WO-A-02095019, is more suitable for treating intervertebral disc and central nervous system than any other commercially available cryoprecipitate e.g. cryoprecipitate that are based on Schwartz et al methodology and which do not retain the fibronectin/fibrinogen ratio present in the original cryoprecipitate or have a ratio equal or lower than 1/12 (Bar et al, 2005) and comprising tranexamic acid and/or bovine aprotinin.

The cryoprecipitate according to the present invention contains certain substances and specific fibronectin/fibrinogen ratio that stimulate attachment, migration and proliferation of notochordal derived cells, a phenomenon which may facilitate in treatment of spine diseases, disorders or conditions such as degenerative intervertebral disc and central nervous system disease, disorder or condition.

The cryoprecipitate according to the invention can comprise a stabilizing agent, for example, arginine or lysine or mixtures of arginine and lysine, or their pharmaceutically acceptable salts. The solution of cryoprecipitate comprises a mixture of proteins such as fibrinogen, Factor VIII, Factor XIII, fibronectin, von Willebrand factor (vWF), vitronectin and the like. The solution of cryoprecipitate can comprise a protease inhibitor other than bovine aprotinin and/or tranexamic acid. Such cryoprecipitate is described in WO-A-9833533 and U.S. Pat. No. 6,121,232, wherein the plasmin and plasminogen are removed as described in EP-B-1,390, 485 and WO-A-02095019. The virus inactivation procedure can be carried out by nanofiltration, solvent/detergent treatment, heat treatment such as, but not limited to, pasteurization, gamma or UVC (<280 nm) irradiation, or by any other method known in the art. The term "infective particle" refers to a microscopic particle, such as micro-organism or a prion, which can infect or propagate in cells of a biological organism. The infective particles can be viral particles.

Viral inactivation procedure can be carried out by adding a molecule to the composition prior to and/or during the purification procedure. The added molecules and their products can be removed by gravitation, column chromatography or any other method known in the art.

The removal of infective particles can be carried out by nanofiltration or by selective absorption methods such as affinity, ion exchange or hydrophobic chromatography. Virus inactivation procedure can be used as the procedure described in WO-A-9114439. A basic principle is treatment of the cryoprecipitate with special detergents and removing the detergent later on from the cryoprecipitate. A multi-step viral inactivation procedure can be carried out. For example, the composition can be subjected to solvent/detergent treatment, heat treatment, selective chromatography and nano filtration. In one embodiment of the invention, the cryoprecipitate is double viral inactivated. According to the invention the cryoprecipitate is a concentrated cryoprecipitate. The cryoprecipitate is concentrated in the range of about a factor of 2 to about a factor of 5. In one embodiment of the invention, the concentration factor is of about 3. In an embodiment of the invention, the cryoprecipitate is concentrated by ultrafiltration to a protein concentration of 60 to 100 mg/ml. The concentration of fibrinogen in the VIPCC can be very high and can be in the range of from about 15 to about 150 mg/ml, of 40 to about 100 mg/ml, or from about 40 to about 60 mg/ml.

As shown in the examples increased fibrinogen levels interferes with attachment, growth and proliferation of nucleus pulposus. However, the high ratio of fibronectin/fibrinogen in the VIPCC seems to mitigate the undesirable effect of fibrinogen present in high levels in VIPCC.

In one embodiment of the invention, the plasma cryoprecipitate is activated. In another further embodiment of the invention the cryoprecipitate is non-activated. The activation procedure can be achieved by mixing said cryoprecipitate with an equivalent volume of an enzyme which is capable to react with fibrinogen to form fibrin. In one embodiment of the invention, the enzyme is thrombin and/or a solution obtainable from snake venom. The thrombin is typically isolated from human beings. It is also possible that the enzyme which is capable to form fibrin is prepared by recombinant methods. The cryoprecipitate according to the invention and/or the activating compound can be supplied as a solution or in a solid form, for example as a lyophilized powder. The solution can be in frozen state.

Activated VIPCC of the invention having the bio-mechanical and physiological properties of the nucleus pulposus can be advantageously used to replace damaged natural tissue of the nucleus pulposus.

The cryoprecipitate can comprise a contrast agent. A "contrast agent" refers to a tracer which is able to make it possible to visualize the anatomy of the spine. The technique which may be used in the method of the invention includes scanning, magnetic resonance imaging, tomography, nanotechnology, digital video, X-ray or any other technique known in the art.

Non limiting examples of contrast agents are organic dyes, food dyes and/or fluorescent dyes. The contrast agent may be chosen from various non-toxic agents, such as iodine. If the spectrum of the contrast agent is not visible to the human eye the agent can be detected by appropriate equipment.

The present invention discloses formation of a two- dimensional matrix suitable for notochord derived cells growth. Also, provided is a three-dimensional scaffold for in vivo and/or in vitro applications including a biocompatible implant for tissue engineering in vivo, as well as for in vitro culturing for cells. The term "tissue engineering" typically refers to the use of a combination of suitable biochemical and physio-chemical factors to restore, replace, maintain, and/or enhance tissue function or a whole organ. The term tissue engineering sometimes is synonymous with the term regenerative medicine.

The term "scaffold" generally refers to a three-dimensional matrix which is able to provide structural integrity and supports a three-dimensional tissue formation, thereby allowing tissue reconstruction.

The scaffold of the invention posses the following properties: non-toxic, biocompatible, biodegradable, allows attachment and migration of notochord derived cells, and enables diffusion of vital cell.

The scaffold of the invention can also be used for delivering and retaining a composition of cells comprising notochord derived cells such as nucleus pulposus cells.

In one embodiment of the invention, said activated cryoprecipitate which is capable of forming a three dimensional scaffold in vivo can be administered by injection into an injured spine, for example, into the nucleus pulposus of a degenerative disc or injured CNS of a subject in need. The in vivo activated cryoprecipitate can be utilized for providing mechanical support, restoring height an/or cell anchoring source to a defective or injured site in situ and/or for providing a matrix into which cells from the injured site can migrate, invade, grow, proliferate, and/or differentiate.

The in vivo forming scaffold can be an injectable material which can be delivered into the injured spine as a liquid through a cannula or needle and harden in the body. In one embodiment of the invention, the in vivo forming scaffold can conform to the shape of the cavity and completely fill the disc space thus enabling a better stability of the vertebral segment.

The cryoprecipitate can be injected simultaneously with an activating compound and harden in vivo. In one embodiment of the invention, the activating component and VIPCC are administered along the injured spinal cord and the activated VIPCC serves as a scaffold for reconstruction of injured and/or ruptured spinal cord caused, for example, by compression of the inervertebral disc.

The VIPCC composition can be used for reconstitution of degenerated intervertebral disc in disease, disorder or condition at different developmental stages. In one embodiment of the invention, the method according to the invention is used for preventing intervertebral disc herniation. In another embodiment of the invention, the method according to invention is for administering to a subject at an early stage of intervertebral disc disease before herniation takes place. In a further embodiment of the invention, the activated cryoprecipitate serves as a scaffold for reconstruction of nucleus pulposus in a subject at advanced stage of intervertebral disc disease and/or spinal cord injury caused, for example, by compression or hemiation of the intervertebral disc.

The VIPCC can be used to restore height and/or to reduce or alleviate discogenic pain. Individuals at high risk of having degenerative disc disease such as patient suffering from osteoporosis can be monitored for changes in disc height and when a decrease is detected, VIPCC of the invention can be administered to restore or elevate disc height.

Alternatively, the method according to the invention comprises the step of excising all or a portion of the nucleus pulposus prior to administering said cryoprecipitate. The removal procedure can be carried out enzymatically by disrupting the extra cellular matrix, mechanically, by using a Nucleotome probe and/or by any other method known in the art.

For example, surgery can be carried out while the patient is deep asleep or pain free by for example, general or local anesthesia, respectively. An incision can be carried out over the site of degeneration, typically the lower back, in the midline. The bone that curves around and covers the spinal cord (lamina) can be removed (laminectomy) and the tissue that is causing pressure on the nerve or spinal cord can be removed. The hole through which the nerve passes can be enlarged to prevent further pressure on the nerve. Sometimes, a piece of bone (bone graft), interbody cages, or pedicle screws may be used to strengthen the area of surgery. The cryoprecipitate of the invention can be introduced trough the hole and/or can be used to coat means used for strengthen the area of surgery.

In one embodiment of the invention, the patient receives local anesthesia and the procedure is a minimal invasive procedure (MIS).

Non limiting examples of mechanical separation techniques include mincing, chopping, slicing, milling, pulverizing, shearing, grinding, trimming, stripping, skinning. Disc cell isolation can be further facilitated with the use of other known separation techniques, such as filters, centrifuges, separation columns, affinity columns, or by any other technique known in the art.

The proteolytic enzymes capable of degrading cartilage tissue include, but are not limited to, serine peptidases, for example, trypsin, chymotrypsin, pancreatic elastase; cystein peptidases, for example, papain chymopapain; aspartic peptidases, for example, pepsin, metallo peptidases, for example, collagenase, gelatinase, pronase, chondroitinase; hyaluronidase and/or alternative chemical materials which would degrade disc material in the same or similar manner, and combinations thereof.

It should be understood that the amount of the pharmacologically suitable solution of enzymes required for the degradation of mammalian disc tissue will vary.

The term "pharmacologically suitable solution" refers to dissolving an effective amount of proteolytic enzymes in a solution. The pH of the solution can be adjusted to a physiologically compatible pH of about 7.40 for maximum activation of the proteolytic enzymes. For better results, the solution can contain all components required to activate the proteolytic enzymes.

The proteolytic enzymes capable of degrading cartilage tissue can be supplied as a solution and/or in a solid form such as lyophilized powder. The solution and/or the powder are sterile, pyrogen-free in a freeze dried state until immediately prior to use. The vial, which contains the lyophilized powder, is typically allowed to warm to room temperature and is reconstituted in a sterile aqueous solution.

As used herein, the term "pyrogen" refers to infective particle, such as a virus, a prion, an endotoxin and/or an exotoxin, which can infect or propagate in cells of a biological organism.

The patient can be positioned laterally and bended forward and the needle or cannula can be positioned selectively in the nucleus pulposus under guidance, for example, scanning, magnetic resonance imaging, tomography, nanotechnology, digital video and/or X-ray, or by any other technique known in the art.

Non limiting examples of guiding agents are non-toxic organic dyes, food dyes and/or fluorescent dyes. If the spectrum of the guiding agent is not visible to the human eye the agent can be detected by appropriate equipment.

Once the location is verified, the proteolytic enzymes solution can be applied such as by injection into the injured area in order to degrade all or a portion of the nucleus pulposus tissue. The digested tissue can be aspirated and placed in a tube. Growth medium such as DMEM/Ham's F12 medium can be added into the suspension.

In another embodiment of the invention, nucleus pulposus tissue is excised using a Nucleotome probe. The patient can be positioned laterally and bended forward and the cannula containing the Nucleotome probe can be inserted under guidance as specified above. The Nucleotome probe has a rounded tip which can resect and aspirate nucleus pulposus tissue from the lumbar disc. The collected nucleus pulposus tissue can be partially or completely digested at 37° C. with proteolytic enzyme solution capable of degrading cartilage tissue as specified above.

The activated VIPCC of the invention that can cure in vivo can be administered with the harvested nucleus pulposus cells, thereby providing an effective construct in which the injected cells can grow in a three-dimensional mode.

In the case that nucleus pulposus cells are treated with proteolytic enzyme, prior to the administering procedure, the proteolytic enzyme solution can be flushed from the dissociated nucleus pulposus cells and/or tissue by adding an effective amount of inactivators and/or removing the proteolytic enzymes by centrifugation and discarding the supernatant phase, or by any other method known in the art.

The harvested dissociated nucleus pulposus cells can be frozen in liquid nitrogen and then stored at −80° C. until use.

Alternatively, the method according to the invention may include, without excluding other possibilities, autologous, allogenic, xenogenic and/or cells harboring recombinant DNA.

The term "autologous" cells refer to cells originally derived from the same individual to which they will be re-implanted.

The term "allogenic" cells refer to cells obtained from the body of a donor of the same species.

"Xenogenic" cells are those isolated from individuals of another species.

The injected cells can comprise a composition of cells comprising cells selected from notochordal derived cells.

Thus, the cryoprecipitate of the invention can be administered into the disc, optionally with notochord-derived cells, such as nucleus pulposus cells.

The population of cells may further comprise annulus fibrosus cells (e.g. from cadaver).

In one embodiment of the invention, the injected cells are nucleus pulposus cells. In a further embodiment of the invention, the cells are from autologous origin. In another further embodiment of the invention, the removal of autologous nucleus pulposus, and cell delivery or re-implantation steps are performed within the same surgical procedure.

The cells to be delivered into the injured spine can be included in the activating component e.g. thrombin, in the cryoprecipitate component, and/or can be in a separated component.

According to one embodiment of the present invention, the cells to be administered into the injured spine can be cultured ex-vivo prior to the administration procedure on a cryoprecipitate comprising a fibronectin/fibrinogen ratio higher than 1/12. In another embodiment of the invention, the ratio is from about 1/11 to about 1/5. In another further embodiment of the invention, the cryoprecipitate contains a fibronectin/fibrinogen relative concentration of from about 1/10 to about 1/5. Yet in another embodiment of the invention, the cryoprecipitate contains a fibronectin/fibrinogen relative concentration of from about 1/10 to about 1/7. Yet in another further embodiment of the invention the fibronectin/fibrinogen ratio is of about 1/7.

The ex-vivo cultured cells can be grown on activated and/or non-activated cryoprecipitate. The activation procedure can be achieved by mixing said cryoprecipitate with an enzyme which is capable to react with fibrinogen to form fibrin. In one embodiment of the invention, the enzyme is thrombin and is added in an equivalent volume to the cryoprecipitate. In another embodiment of the invention, the enzyme is a solution obtainable from snake venom. The thrombin can be isolated from plasma of human beings or mammals and/or prepared by recombinant methods. The cryoprecipitate of the invention and/or the enzyme capable to form fibrin can be supplied as a solution or in a solid form, for example as a lyophilized powder. The solution can be in frozen state.

As used herein, "ex-vivo" cell culture refers to culturing cells outside of the body. Ex-vivo cell culture includes cell culture in vitro, e.g., in suspension, or in single or multi-well plates. Ex-vivo culture also includes co-culturing cells with different cell types, and culturing in or on two- or three-dimensional matrices.

In another aspect, the invention relates to the use of a kit for treating a spine disease, disorder or condition such as for a degenerative intervertebral disc. The kit comprises a first container comprising a VIPCC according to the invention, and a second container comprising an enzyme capable of forming fibrin when it reacts with fibrinogen. According to the invention tranexamic acid and bovine aprotinin are absent from the kit. In one embodiment of the invention, VIPCC in which plasminogen and plasmin have been lowered to equal or less than 15 μg/ml like for example 5 μg/ml or less is used.

In another embodiment of the invention, the kit is directed for administering therapeutic solutions in the emergency treatment of spine and cord injury or other mitigation of injured axons into an injured central nervous system.

The kit can also comprise a contrast agent, for example, in order to localize the site of administration and to enhance imaging. The contrast agent can be included in the container comprising the cryoprecipitate component, in the container comprising the enzyme component and/or in a separated container. In one embodiment of the invention, the contrast agent is formulated with the cryoprecipitate. In another embodiment of the invention, the contrast agent is formulated with the enzyme capable of forming fibrin. Examples of contrast agents include, but are not limited to, organic dyes, food dyes and/or fluorescent dyes. The contrast agent may be chosen from various non-toxic agents, such as iodine. The techniques which may be used to detect the contrast agent include scanning, magnetic resonance imaging, tomography, nanotechnology, digital video, X-ray or any other technique known in the art. If the spectrum of the visualization agent is not visible to the human eye the agent can be detected by appropriate equipment.

In another aspect the invention relates to a kit comprising: a first container comprising a VIPCC according to the invention, a second container comprising an enzyme capable of forming fibrin when it reacts with fibrinogen, and a third container comprising a proteolytic enzyme capable of degrading extra cellular matrix such as proteolytic enzymes capable of degrading cartilage tissue selected from the group consisting of serine peptidases, cystein peptidases, aspartic peptidases, metallo peptidases, hyaluronidase and combinations thereof In one embodiment of the invention, the proteolytic enzyme is selected from the group consisting of trypsin, chymotrypsin, pancreatic elastase, papain chymopapain, pepsin; collagenase, gelatinase, pronase chondroitinase, hyaluronidase and/or alternative chemical materials which would degrade disc material in the same or similar manner, and combinations thereof. The kit can also comprise a contrast agent, for example, iodine, as described above.

The cryoprecipitate and/or the enzyme capable of forming fibrin and/or the proteolytic enzyme and/or the contrast agent can be provided in the spinal intervertebral and the central nervous system reconstruction kits as a solution and/or in a solid form, for example, as lyophilized powder. The solution can be in frozen state. The kits can comprise instruction for use. The kits can also comprise a needle such as a spinal needle including for example a curved spinal needle. A spinal cannula may alternatively be used. A single, dual or multi-barrel syringe, or other fibrin sealant delivery device, may be included in the kit.

Subject matter of the present invention relates to the use of a scaffold suitable for treating a spine disease, disorder or condition such as for regeneration of spinal intervertebral disc and central nervous system. The scaffold is prepared using a cryoprecipitate according to the invention and an activating compound. According to the invention the VIPCC composition does not contain tranexamic acid and/or bovine aprotinin.

The components of the spine reconstruction kits, or formulations, can be in separated recipients such as syringes which can be applied in any order, for example, the components can be applied simultaneously or one after the other and a scaffold is formed when the components are mixed.

In one embodiment of the invention, the separated recipients can be configured for applying said cryoprecipitate, an enzyme capable of forming fibrin, and notochordal derived cells. In another embodiment of the invention, the notochordal derived cells can be combined with said cryoprecipitate and/or with the enzyme capable of forming fibrin prior to mixing the components.

According to the invention, the components of the kit can be provided as a solution and/or in a solid form. The solution can be in frozen state.

Another object of the invention is establishing a tissue or cell bank of notochordal derived cells grown in a scaffold as specified above.

In one embodiment of the invention, the tissue or cell bank can be used in repair and/or regeneration of intravertebral disc and central nervous system reconstruction. In one embodiment of the invention, the notochordal-derived cells are nucleus pulposus cells.

According to the invention the tissue or cell bank can comprise autologous, allogenic, xenogenic and/or cells harboring recombinant DNA.

As used herein, "tissue or cell bank" refers to a tissue or cell bank developed by a method which allows the establishment of notochordal derived cells suitable for repairing, regenerating and/or replacing damaged spine, for example, intravertebral disc tissue and central nervous system tissue such as axons and motorneurons. The cells in said tissue or cell bank can maintain their characteristics, e.g., biochemical, morphological and/or physical properties, necessary to perform specialized function. Advantageously, the cells have the ability to proliferate and/or differentiate into nucleus pulposus cells on two dimentional mode- or three-dimensional constructs.

Another aspect of the invention relates to a vehicle which can advantageously be used for delivering a composition of cells comprising notochordal derived cells into a damaged spine such as damaged intervertebral disc and central nervous system tissue because the cryoprecipitate according to the invention provides a suitable scaffold on which the notochordal derived cells can attach, migrate, grow, divide, maintain their function, morphology and/or differentiate. The vehicle or construct comprises cryoprecipitate according to the invention and notochordal derived cells. Tranexamic acid and bovine aprotinin are excluded from the cryoprecipitate composition. In one embodiment of the invention, the notochordal-derived cells are nucleus pulposus cells. The cell delivery vehicle can further comprise annulus fibrosus cells.

The term "vehicle" refers to a mean for delivery of cells into a specific tissue in vivo. Viable cells are incorporated into the cell delivery vehicle according to the invention and administered into the damaged spine such as intervertebral disc or central nervous system allowing reconstitution, repair or restoration of the damaged site. The cell delivery device can be in a liquid state or as a cured construct.

The delivered cells can be autologous, allogenic, xenogenic and/or cells harboring recombinant DNA. Disc cells cultured in monolayer tend to de-differentiate and loose their typical cell phenotype (Benya and Shaffer. "Dedifferentiated chondrocytes reexpress the differentiated collagen phenotype when cultured in agarose gels". Cell. 1982; 30:215-224. According to the invention it has been found that annulus fibrosus cells and notochordal derived cells, e.g. nucleus pulposus cultured in cryoprecipitate of the invention maintain their phenotype and provide a matrix which can be used in an in vitro and in vivo expansion for reconstructive surgery of intervertebral cartilage and central nervous system. It was found according to the present invention that VIPCC has chondro-conductive components which stimulate cell attachment and proliferation of annulus fibrosus and nucleus pulposus cells seeded in culture dish coated with VIPCC. The findings according to the invention show that no detectable morphological changes or damage was done during sub-culturing or trypsinization. Moreover, even though the cells migrated throughout the culture dish a differential attachment to VIPCC and fibronectin was observed. The results demonstrate that fibronectin, recognized as an agent which promotes cellular adhesion, is a fundamental component in the VIPCC and needs to be at a specific ratio with fibrinogen to facilitate the attachment and proliferation of nucleus pulposus chondrocytes.

Thus, it is also subject matter of the invention to provide a method for facilitating growth, proliferation, differentiation and/or maintenance of notochordal derived cells comprising contacting the population of cells from the notochordal derived cells with the VIPCC according to the invention. Yet in another embodiment of the invention, the notochordal derived cells are nucleus pulposus cells. The contacting of the nucleus pulposus with the cryoprecipitate can be carried ex vivo and/or in vivo.

The VIPCC can be activated or non-activated. The contacted cells can be autologous, allogenic, xenogenic and/or cells harboring recombinant DNA.

The cryoprecipitate of the present invention can have conductive and inductive capabilities.

The conductive or inductive capability of said cryoprecipitate of the present invention can be determined following use of the cryoprecipitate and consequently assess enhancement of adhesion, migration, proliferation, and/or differentiation of the cultured annulus fibrosus and notochordal derived cells e.g. nucleus pulposus cells. Assessments of these properties are carried out by any technique known in the art, for example, proliferation by using a haemacytometer or by Hematoxylin and Eosin staining, differentiation, by measuring chondroitin sulfate expression, migration by using migration test as exemplified below.

As used herein, the term "conductive" refers to the ability of the activated cryoprecipitate to serve as a scaffold on which specific cells can attach, grow, migrate, proliferate and/or differentiate, including "chondro-conductive" or "neuro-conductive" etc.

As used herein, the term "inductive" refers to the capacity of the cryoprecipitate to stimulate specific cells to attach, grow, migrate, proliferate and/or differentiate, including "chondro-inductive", or "neuro-inductive" etc.

Another term use for "conductive" is "chemotactic". The term "chemotactic" refers to physiological responses that result in a characteristic movement or orientation of cell towards a chemical stimulus.

An intradiscal or intrathecal injection may result in a change in the typical structure of the nucleus pulposus population e.g. necrotic damage, pyknotic nuclei and karyolysis. It was found according to the invention that this problem can be solved or diminished by including the cryoprecipitate according to the invention in the formulation to be administered to the injured spine, for example, degenerative disc and injured central nervous system.

The kit, the formulation, the scaffold, the tissue or cell bank and/or the vehicle according to the invention, can comprise one or more additives such as, but not limited to: biochemical factors which support the expansion of cells while maintaining their commitment to differentiate, therapeutic agents (such as antibiotics, anti-inflammatories), analgesics, anti-tumor drugs, growth factors, proteins, hormones, cartilage inducing factors, proteoglycans such as aggrecan, type I and II collagen, oxygen-containing components, enzymes and the like.

One or more of these components can be included in the cryoprecipitate component, in the activating component e.g. thrombin, and/or can be in a separated component.

The kit, the formulation, the scaffold, the tissue or cell bank and/or the vehicle to be administered to a subject in need for the reconstitution of the central nervous system can comprise Rho Kinase Inhibitors such as, for example, Cethrin®, Y-27632, C3 etc.

Yet another object of the invention is accomplished by providing a method for treating a spine disease, disorder or condition such as intervertebral disc and central nervous system disease comprising administering to a subject in need a kit, a VIPCC, cells from a tissue or cell bank and/or a vehicle according to the invention.

Another aspect of the invention relates to the use of a viral inactivated-plasma activated cryoprecipitate concentrate according to the invention for treating a spine disease, disorder or condition. According to the invention, bovine aprotinin is absent from the cryoprecipitate composition. In one embodiment of the invention, said cryoprecipitate comprises an initial fibronectin/fibrinogen relative concentration of about 1/10 to about 1/5, or from about 1/10 to about 1/7.

The cryoprecipitate can be used for treating an intervertebral disc disease, disorder or condition, or an injured CNS.

It was found according to the invention that activated-VIPCC substantially restored IVD height as compared to PBS injected discs. Thus, the activated-VIPCC of the invention can function as matrix or device with suitable mechanical properties which can advantageously serve to substantially restore the normal disc structure, height and allow disc space retention under load.

Therefore, in another aspect, the invention relates to the use of VIPCC according to the invention for elevating or restoring intervertebral disc height. For example, activated VIPCC according to the invention can be injected in black disc to restore height of the disc. In earlier stages of disc degeneration, when nucleus pulposus cells are still present in the disc, VIPCC of the invention will advantageously elevate disc height and serve as scaffold for the reminding nucleus pulposus cells. In this case tranexamic acid and bovine aprotinin are absent from the cryoprecipitate concentrate.

In one embodiment of the invention, said cryoprecipitate comprises an initial fibronectin/fibrinogen relative concentration of about 1/10 to about 1/5, or from about 1/10 to about 1/7 such as in the ratio of about 1/7.

The kit, formulation, tissue or cell bank and/or vehicle according to the invention for preventing and/or treating injured spine can optionally include autologous, allogenic, xenogenic annulus fibrosus cells and/or annulus fibrosus cells harboring recombinant DNA.

The disclosure of ranges in the description of the invention is easily understood by the skilled person. It means the disclosure of continuous values and figures between the limits of the ranges, including the limiting figures and values. For example, if a range is given of from 1/11 to 1/5, it is meant at least 1/11, 1/10, 1/9, 1/8, 1/7, 1/6 and/or 1/5 with all combinations of intermediate sub ranges such as 1/11 and 1/10, 1/11-1/9, 1/11-1/8, 1/11-1/7, 1/11-1/6, 1/11-1/5 or 1/10-1/9, 1/10-1/8, 1/10-1/7, 1/10-1/6, 1/10-1/5 and so on.

The disclosure of applications, patents and publications, cited above or below, is hereby incorporated by reference.

The following examples are illustrative but not limiting.

EXAMPLES

Example 1

Preparation of Annulus Fibrosus and Nucleus Pulposus Chondrocytes

This example illustrates preparation of chondrocyte cell culture. Pig lumbar spine (L1-L6) was isolated 12 hours after slaughter (transported at 4° C.), sterilized with septal scrab for 10 min and soaked in 70% ethanol for 5 min. The muscle and other connective tissues were removed and each vertebral body was dissected in the middle so that isolated intervertebral discs (IVDs) could be obtained. The isolated IVDs were then dipped in graduated cylinder containing PBS with 200 µg/ml sodium azide for a few seconds. Followed by dipping in sterile PBS containing 10 U/ml penecillin, 0.1 mg/ml streptomycin, 2.5 µg/ml amphothericin, 50 µg/µl gentamycin, 10 µg/ml vancomycin, 65.6 µg/ml cephalosporin and 10% fetal bovine serum (FBS). Specimens were then transferred to a sterile laminar flow and the remaining procedure was done under sterile conditions.

Each IVD was cut in half using a scalpel and the nucleus pulposus tissue was carefully separated and placed in a 97 mm cell culture dish. The nucleus pulposus tissue was rinsed three times in PBS supplemented with the above mentioned antibiotics and FBS to remove residual debris. Then, the nucleus pulposus tissue was subjected to gentle digestion (for 3 hours) by a collagenase solution (Sigma cat No C-6885; 3 mg/ml in 1:1 mixture of DMEM/Ham's F12 medium (Biological industries) supplemented with 10 U/ml penicillin, 0.1 mg/ml streptomycin, 0.25 µg/ml amphothericin, 100 mg/µl gentamycin, 10 µg/ml vancomycin and 6.56 µg/ml cephalosporin) for 3 h at 37° C. in a humidified atmosphere of 5% $CO_2$.

Prior to the digestion procedure the collagenase solution was transferred through 0.45 µm filter (Millipore SLHV033RS).

The digested tissue was filtered through sterile gauze and centrifuged at 800 g for 5 min. After centrifugation, the supernatant phase was discarded, and cells were re-suspended in 2 ml of DMEM/Ham's F12 supplemented with 10 U/ml penicillin, 0.1 mg/ml streptomycin, 0.25 µg/ml amphothericin, 100 mg/µl gentamycin, 10 µg/ml vancomycin and 6.56 µg/ml cephalosporin.

The annulus fibrosus tissue was removed from the opened IVDs, placed in a 97 mm cell culture dish and rinsed twice in PBS containing 10 U/ml penicillin, 0.1 mg/ml streptomycin, 2.5 µg/ml amphothericin, 50 µg/µl gentamycin, 10 µg/ml vancomycin, 65.6 µg/ml cephalosporin and 10% FBS. Annulus fibrosus tissue was minced to small pieces (3-5 mm) using a scalpel. The minced tissue was incubated overnight at 37° C. in a humidified atmosphere of 5% $CO_2$. After incubation, the tissue was digested with a collagenase solution (prepared as above-mentioned) in 5% $CO_2$ at 37° C. for 5 hours. After digestion was completed, the cell suspension was transferred through sterile gauze. Afterwards, the suspension was centrifuged at 800 g for 5 min and the pellet containing the annulus fibrosus chondrocytes was re-suspended in 2 ml of fresh DMEM/Ham's F12 medium (supplemented as mentioned above).

Example 2

Effect of Thrombin, Viral Inactivated-Plasma Cryoprecipitate Concentrate (VIPCC) and Components Thereof on Annulus Fibrosus Cell Attachment and Proliferation

The following example was carried out in order to investigate the effect of thrombin, VIPCC, and components thereof on annulus fibrosus cell attachment, proliferation and chemotaxis. For this purpose, a 97 mm plastic culture dish was coated at the circumference with 80 µl of the following solutions: VIPCC (BAC; Omrix, I L; prepared as described in EP-B-534,178, wherein the plasmin(ogen) was removed as described in EP-B-1,390,485); purified human fibrinogen (Enzyme research; cat No FIB1 2800L); thrombin (Omrix, I L; prepared as described in U.S. Pat. No. 5,143,838 and in EP-B-378,798); and human serum albumin (Sigma; cat No A7030) see FIG. 1. Each solution contained 5-20 µg/ml total protein. Dilutions were done in saline. The fibrinogen content in the purified fibrinogen coating and in the VIPCC coating was about 8 µg. The solutions were left to dry in a laminar flow under sterile conditions. Afterwards, 150 µl annulus fibrosus cells ($5 \times 10^6$) suspended in growth medium (DMEM/Ham's F12 supplemented with the above mentioned antibiotics and 10% FBS) were placed in the center of the dish (FIG. 1 Origin), the dish was covered and incubated overnight at 37° C. in a humidified atmosphere of 5% $CO_2$. After incubation, the medium was discarded and replaced by 10 ml growth medium (DMEM/Ham's F12 medium supplemented with antibiotics and 10% FBS), and the culture dish was incubated for additional 14 days.

Histological assessments of the above two dimensional cultures were performed by Hematoxilin and Eosin staining method. Briefly, the cultured chondrocytes were fixed with 95% ethanol for 15 min, washed in $H_2O$ and exposed to Hematoxylin solution Gill NR1 (Sigma; cat No GHS116) for 3 min. Then the cultures were washed in $H_2O$, counterstained with Eosin Y (Sigma; cat No E4382) for 30 seconds and rinsed in 95% Ethanol and $H_2O$. Afterwards, the cells were washed in $H_2O$ three times and analyzed macroscopically and microscopically. As seen in FIG. 1, annulus fibrosus cells seeded at the center of a culture dish migrated evenly throughout the whole field, but showed better attachment and proliferation on coated spots comprised of VIPCC as compared to uncoated plates or human fibrinogen, thrombin, or human serum albumin coated spots. The results indicate that VIPCC has chondro-conductive components which stimulates annulus fibrosus cell attachment and proliferation and may facilitate in reconstruction of degenerative intervertebral disc.

Example 3

Effect of Trypsinization Procedure and/or Passage on VIPCC Mediated Annulus Fibrosus Cell Attachment and Proliferation

Passage number refers to the "age" of a cell line or to the number of times the cells have been sub-cultured. Some cell lines may exhibit morphological changes after passages. In addition, cell culture procedures used for sub-culturing such as trypsinization can damage cell membranes resulting in poor attachment, clumping or "ragged" looking membranes. The present study was aimed to determine the effects of trypsinization and/or passage on VIPCC-mediated annulus fibrosus chondrocytes cell attachment and proliferation. For this purpose, chondrocytes derived from the annulus fibrosus (as described in Example 1) were isolated and 500 µl containing $0.625 \times 10^5$ cells were placed in a well of an uncoated 24-well plate. The culture was incubated for 11 days in a humidified atmosphere of 5% $CO_2$ at 37° C. After incubation, the cells were enzymatically dissociated by adding 100 µl trypsin (Trypsin-EDTA Biological Industries, 03-050-1A) to each well at 37° C. for 5 min. The dissociated chondrocytes were collected from three wells into a vial and the cell suspension was centrifuged at 800 g for 5 min. The supernatant phase was discarded, the cells were re-suspended in 200 µl DMEM/Ham's F12 medium (supplemented with antibiotics and 10% FBS) and placed in the center of a 97 mm plastic culture dish coated at the circumference with 80 µl drops of the following solutions: VIPCC containing 6.4 µg total protein (from which 4.7 µg is fibrinogen), 3 µg purified human fibrinogen, 0.18 µg fibronectin (produced according to Miekka et al. "Rapid methods for isolation of human plasma fibronectin". Thromb Res. 1982; 27:1-14), and a purified fibronectin/human fibrinogen mixture in a concentration of 0.3:2.7 µg, respectively (approx. ratio of 1/10). The culture was incubated in 5% $CO_2$ at 37° C. for 24 hours, washed twice in a growth medium to remove unattached cells, and 10 ml of DMEM/Ham's F12 medium (supplemented with antibiotics and 10% FBS) was added. The cultures were incubated for additional 9 days. Morphological assessment was performed by staining the cells with Hematoxylin and Eosin solutions, followed by macroscopic and microscopic observation.

Figure 2:
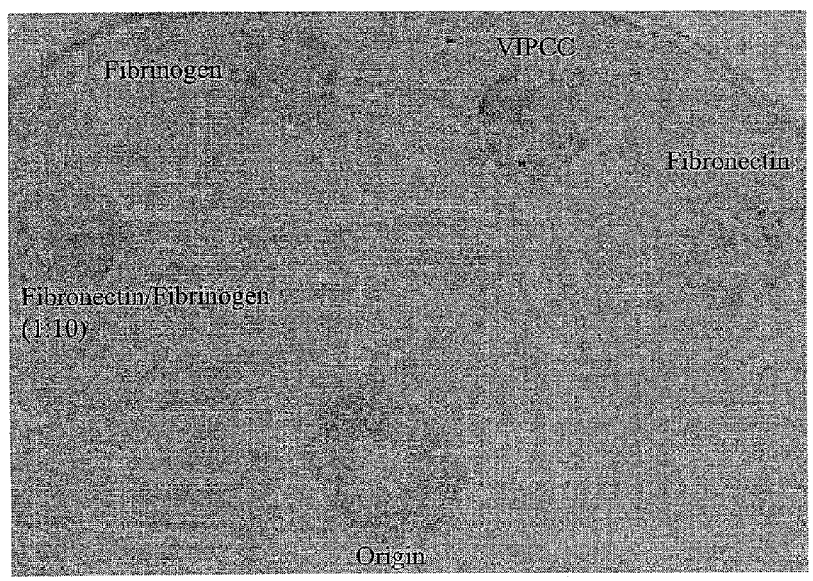
FIG. 2: shows the effects of trypsinization procedure and/or passage on cell attachment and proliferation of annulus fibrosus cells. Dissociated annulus fibrosus cells were placed in the center of a 97-mm plastic culture dish coated at the circumference with VIPCC, fibrinogen, fibronectin, and purified fibronectin/fibrinogen mixture (1:10). Cell attachment was assessed after 9 days by Hematoxylin and Eosin staining.

The results show that sub-culturing or trypsinization procedure does not result in any morphological changes of the annulus fibrosus cells. Moreover, it is apparent that the cells migrated throughout the culture dish, but a differential attachment to the VIPCC and fibronectin coating was observed (FIG. 2). The results demonstrate that fibronectin, recognized as an agent which promotes cellular adhesion, is a fundamental component in the VIPCC which stimulates the attachment and proliferation of chondrocytes cells.

Example 4

Effect of Fibrinogen/Fibronectin Ratio on Annulus Fibrosus and Nucleus Pulposus Cell-Attachment and Proliferation

The above example illustrates the role of fibronectin present in the VIPCC component in stimulating migration, proliferation and attachment of the annulus fibrosus chondrocytes. The present experiment was designed to investigate the effect of different ratios of fibronectin/fibrinogen mixtures on attachment and proliferation of nucleus pulposus and annulus fibrosus chondrocyte cells. For this purpose, a well of a twenty-four-well plate was coated with 200 µl of one of the following components: 0.626 µg purified fibronectin; 10 µg purified human fibrinogen (fgn); or with a fibronectin and fibrinogen mixture in the following concentration: 0.626 µg: 3.13 µg, 0.626 µg: 6.26 µg, or 0.626 µg: 12.52 µg (ratios of 1/5, 1/10 and 1/20, respectively). Thus, in the components the amount of fibronectin was kept constant, while the amount of fibronectin was incremented.

The solutions were left to adhere to the wells in a laminar flow under sterile conditions. After 3 hours, excess solution was removed and the plate was turned upside down for an additional 2 hours incubation to allow drying. 500 µl freshly isolated nucleus pulposus or annulus fibrosus cells were suspended in DMEM/Ham's F12 medium (supplemented with the above mentioned antibiotics and 10% FBS) and seeded into the above coated wells at a concentration of $6 \times 10^4$ cell per well. The cultures were incubated in a humidified atmosphere of 5% $CO_2$ at 37° C. for 5 and 12 days.

Histological assessments of the above two-dimensional cultures were performed after 5 and 12 days in vitro. The cultured chondrocytes were fixed and exposed to Hematoxylin and Eosin Y solutions as specified above. Afterwards, the culture was stained with Crystal Violet (1 g in 100 ml of Acetic Acid) for 10 min and washed in $H_2O$.

In order to quantify the level of cell attachment, the color was extracted from the cells with 100 µl 70% ethanol for 10 min. 75 µl aliquots were transferred to a 96-well plate and the absorbance was measured in a spectrophotometer at a wavelength of 590 nm. The absorbance of cells grown on fibronectin coated wells was considered as 100% cell attachment.

Figure 3A:
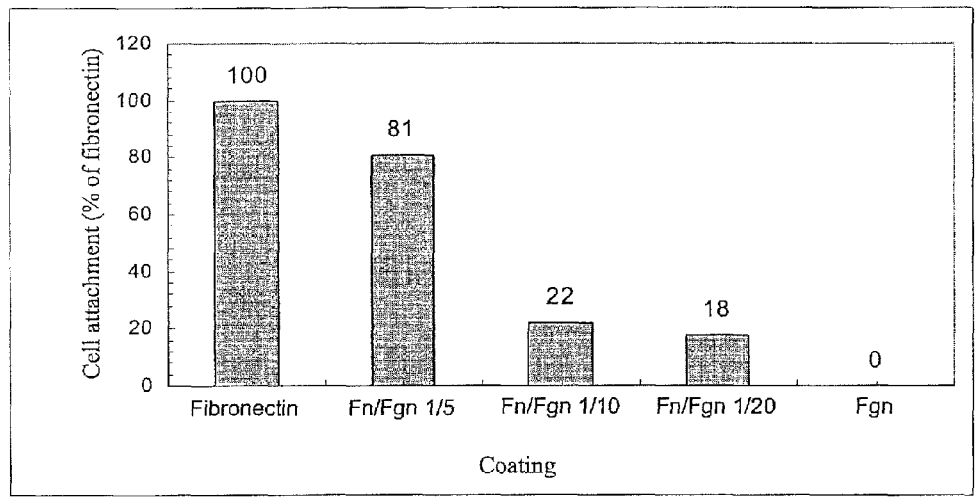
FIGS. 3A-3B: show nucleus pulposus (A) and annulus fibrosus (B) cell-attachment on different coatings. The results obtained are expressed as a fold cell attachment to fibronectin coatings in the same experiment (100%). Fn-fibronectin; Fgn-fibrinogen.

Results of nucleus pulposus and annulus fibrosus cell attachment after 5 days in culture on the different coatings are presented in FIGS. 3A and B, respectively. Surprisingly, it was found that in contrast to annulus fibrosus cell attachment nucleus pulposus cell attachment was affected by the different coatings. The results show that an increase in fibrinogen concentration significantly decreased nucleus pulposus cell attachment in a dose depended manner. While an increase in fibronectin/fibrinogen ratio lead to the opposite outcome (FIG. 3A), for example, a purified mixture of fibronectin/fibrinogen in a ratio of 1/5 showed a higher rate of nucleus pulposus cell attachment as compared to purified mixtures in ratios of 1/10 and 1/20 (FIG. 3A). These results demonstrate that fibronectin/fibrinogen in a ratio of about 1/5 is more suitable for cell-attachment and proliferation of nucleus pulposus cells than mixtures comprising a lower fibronectin/fibrinogen ratio.

These results indicate the key role of fibronectin/fibrinogen ratio in nucleus pulposus cell attachment and demonstrate the advantage of using a high level ratio of fibronectin/fibrinogen for nucleus pulposus cells.

The effect of VIPCC which contains a fibronectin/fibrinogen ratio in the range of 1/10-1/5 and a purified mixture of fibronectin/fibrinogen at a ratio of 1/10 in nucleus pulposus and annulus fibrosus cell proliferation was evaluated. Cell proliferation was calculated by subtracting the percentage of cell attached on day 5 from the percentage of cell attached on day 12. The results are based on the measurements carried out in the above experiment. The results are summarized in Table 1 which shows the percentage of attached cells after 5 and 12 days of culture.

TABLE 1

The percentage of nucleus pulposus and annulus fibrosus attached cells on VIPCC and fibronectin/fibrinogen mixture (1/10) coatings.

|  | Day of culture | A purified mixture of fn/fgn (1/10) Attached cells (%) | VIPCC |
| --- | --- | --- | --- |
| Nucleus Pulposus | 5 | 22 | 56 |
|  | 12 | 14 | 77 |
| Annulus Fibrosus | 5 | 65 | 62 |
|  | 12 | 71 | 88 |

The results in Table 1 are presented as percentages of attached cells relative to attached cells in fibronectin coating in the same experiment (considered as 100%).

Figure 3B:
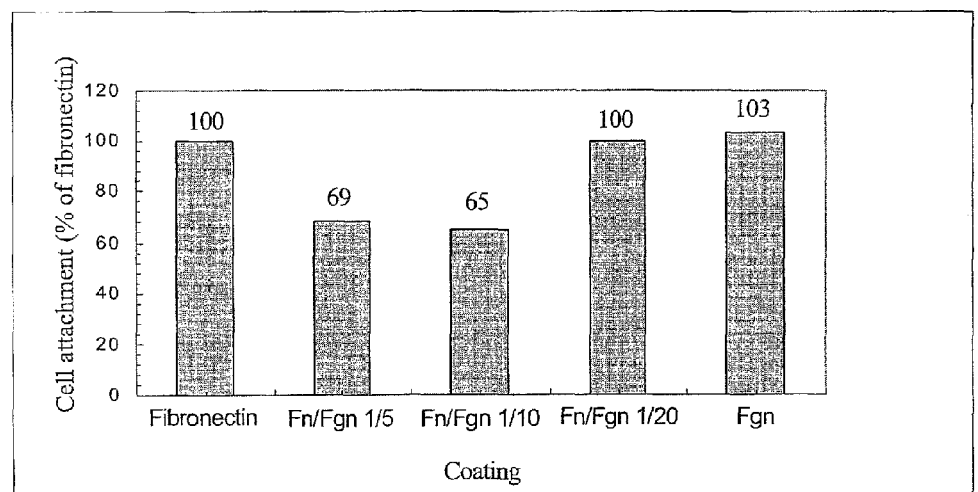

The results obtained indicate that on day 5 nucleus pulposus cell attachment was significantly higher on VIPCC coating as compared to a purified mixture of fibronectin/fibrinogen in a ratio of 1/10 (56% and 22% cell attachment for VIPCC and the purified mixture, respectively) (FIG. 3A and Table 1). In contrast, cell attachment of annulus fibrosus chondrocytes was similar on both coatings (62% and 65% cell attachment for VIPCC and the purified mixture, respectively) (FIG. 3B and Table 1).

In addition the results obtained on day 12 show that annulus fibrosus cell culture seeded on VIPCC coating exhibited a significant increase in cell number (62 and 88% on day 5 and 12, respectively; Δ=26%) as compared to a purified fibronectin/fibrinogen mixture coating (65 and 71% on day 5 and 12, respectively; Δ=6%). Nucleus pulposus cell culture showed a similar, though a pronounced effect. VIPCC coating resulted in an increase of 21% in cell number (56 and 77% on day 5 and 12, respectively), whereas fibronectin/fibrinogen mixture coating resulted in a decrease of attached cells (22 and 14% on day 5 and 12, respectively; Δ=−8%). These results demonstrate that cell proliferation of nucleus pulposus and annulus fibrosus cells was higher on a VIPCC coating than on a coating composed of purified fibronectin and fibrinogen mixture and that nucleus pulposus chondrocytes were more affected by the different coatings.

Example 5

The Effect of VIPCC and Mixtures of Purified Fibronectin/Fibrinogen on Cultured Nucleus Pulposus The effect on nucleus pulposus cell attachment and viability by the different concentrations of fibronectin and fibrinogen mixture was further evaluated using the XTT assay. The assay is based on the ability of viable cells to reduce 2,3-Bis (2-methoxy-4-nitro-5-sulfophenyl)-2H-tetrazolium-5-carboxanilide (XTT) from a yellow tetrazolium salt to a soluble orange formazan compound.

Nucleus pulposus cells were prepared using the same procedure described in Example 1. A flat bottom 96-well plate was coated with 30 µl of one of the following solutions: 0.626 µg purified fibronectin, 10 µg purified human fibrinogen, diluted VIPCC (contains about 1.57 µg fibronectin and 10 µg fibrinogen), and fibronectin/fibrinogen mixture (0.626 µg: 6.26 µg; 1/10). The solutions were left to dry in a laminar flow under sterile conditions and then the 100 µl cell suspension was dispensed into the pre-coated wells at a density of $1\times10^4$ cells per well. Uncoated wells served as control group. After a 4 h incubation period, the growth medium (DMEM/Ham's F12 medium supplemented with the above mentioned antibiotics and 10% FBS) was replaced with fresh medium to remove unattached cells. The cultures were incubated in a humidified atmosphere of 5% $CO_2$ and 95% air at 37° C. for 24 hours. At the end of the incubation period, 50 µl of XTT reagent (XTT-Cell Proliferation Kit; Biological industries; cat No 20-300-1000) was added to each well, and the cultures were placed in an incubator at 37° C. for 4 hours. The color developed was read by a spectro-ELISA reader according to the manufacturer's protocol. The supernatant was discarded and fresh growth medium was added. The assay was repeated 5 days later. The absorbance intensity is proportional to the amount of metabolic active cells. Results are presented as percentage of metabolic active cells relative to metabolic active cells in fibronectin coating (100%).

Figure 4:
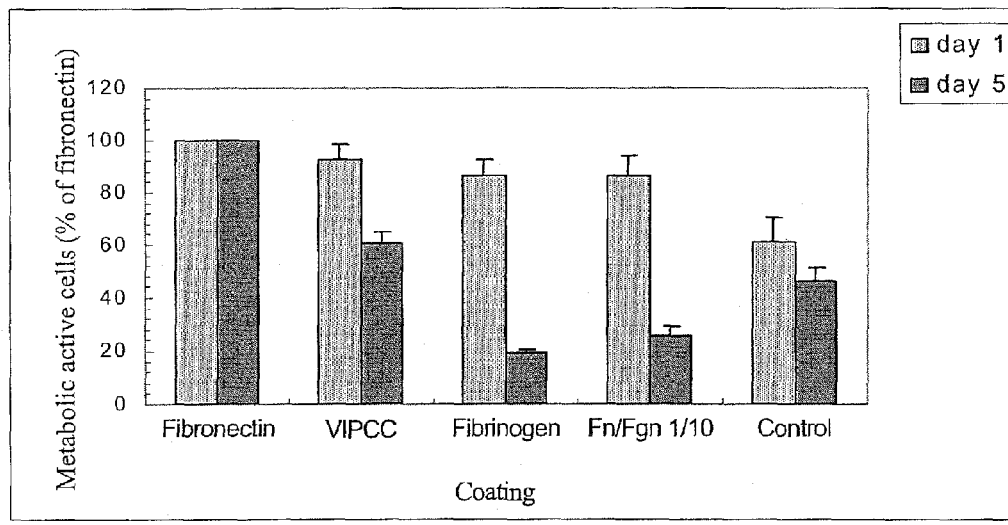
FIG. 4: shows levels of metabolic active nucleus pulposus cells on day 1 and 5 in culture on different coatings. The results are presented as percentage of absorbance intensity in fibronectin coating (100%). VIPCC- viral inactivated-plasma cryoprecipitate concentrate; Fn-fibronectin; Fgn-fibrinogen.

As seen in FIG. 4, fibrinogen coating resulted in a significant decrease in the level of nucleus pulposus metabolic active cells as compared to fibronectin coating (86.4 and 19.6% on day 1 and 5, respectively; Δ=−66.8%). A VIPCC coating, which comprises the same fibrinogen content and a fibronectin/fibrinogen ratio in the range of 1/5-1/10 and a purified fibronectin/fibrinogen mixture at a ratio of 1/10 were able to mitigate the decrease in metabolic active cells observed in the fibrinogen coating. This effect was particularly pronounced in the VIPCC coating. These results confirm the previous results and show the advantages of using VIPCC as a coating for nucleus pulposus cells instead of a pure fibronectin/fibrinogen mixture. Thus, a scaffold for tissue engineering of nucleus pulposus prepared with activated VIPCC may be superior to those prepared with activated pure fibronectin/fibrinogen.

Example 6

Effect of Fibronectin and Fibrinogen Levels on the Percentage of Metabolically Active Nucleus Pulposus and Annulus Fibrosus Cells The present study was aimed to determine the effect of fibrinogen and fibronectin levels on the percentage of metabolically active cultured nucleus pulposus and annulus fibrosus cells. For this purpose, cells derived from the nucleus pulposus and annulus fibrosus were prepared as described in Example 1. A flat bottom 96-well plate was coated with 30 µl fibronectin/fibrinogen-coating. The coating was composed of a constant amount of fibronectin (0.626 µg) and increasing amounts of purified fibrinogen as follows: 0, 3.13 (a ratio of 1/5), 6.26 (a ratio of 1/10), 12.5 (a ratio of 1/20) and 146 µg (a ratio of 1/233). Another set of experiments were done on fibronectin/fibrinogen-coating composed of a constant and high amount of fibrinogen (9.125 µg) and increasing amounts of purified fibronectin as follows: 0.0313 (a ratio of 1/291), 0.042 (a ratio of 1/217), 0.0626 (a ratio of 1/145) and 0.125 µg (a ratio of 1/73).

The solutions were left to dry in a laminar flow under sterile conditions and 100 µl cell suspension (containing $1\times10^4$ cells per well for both cell preparations) was placed in the wells.

The culture was incubated for 4 h and the growth medium (DMEM/Ham's F12 medium supplemented with the above mentioned antibiotics and 10% FBS) was replaced to remove unattached cells. The cultures were incubated for additional 24 hours in a humidified atmosphere of 5% $CO_2$ and 95% air at 37° C. The effect of fibrinogen on cell attachment was assessed at days 7, 10-13 and 16 by the XTT assay as described above. The absorbance intensity is proportional to the amount of metabolic active cells. The results are presented as percentage of fibronectin absorbance intensity (100%). Data are presented as mean±S.D. of at least three separated experiments (in each experiment cells were harvested from three different pigs vertebrate).

Figure 5A:
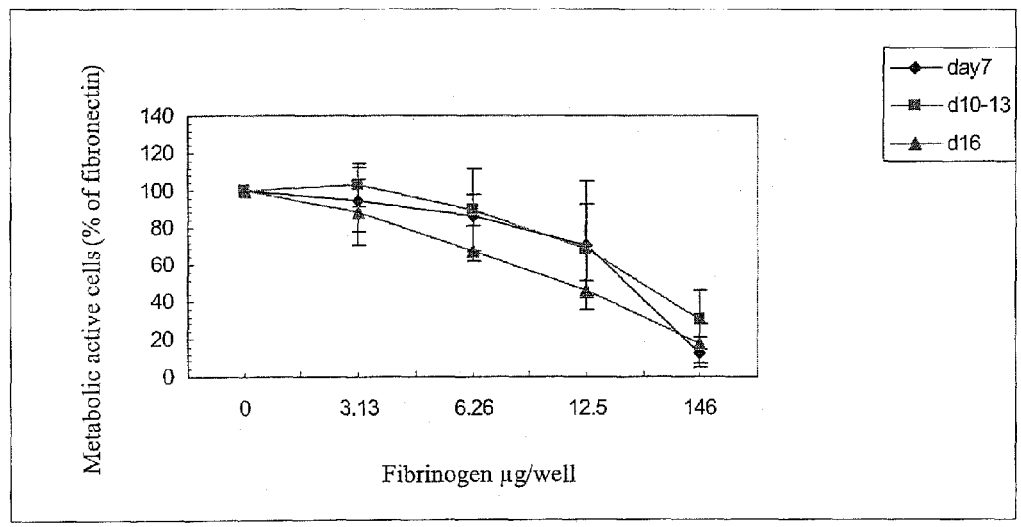
FIG. 5: shows levels of metabolic active nucleus pulposus culture on constant amount of fibronectin and increased amount fibrinogen in the coating matrix (A) and on constant amount of fibrinogen and increased amount fibronectin in the coating matrix (B).
Figure 5B:
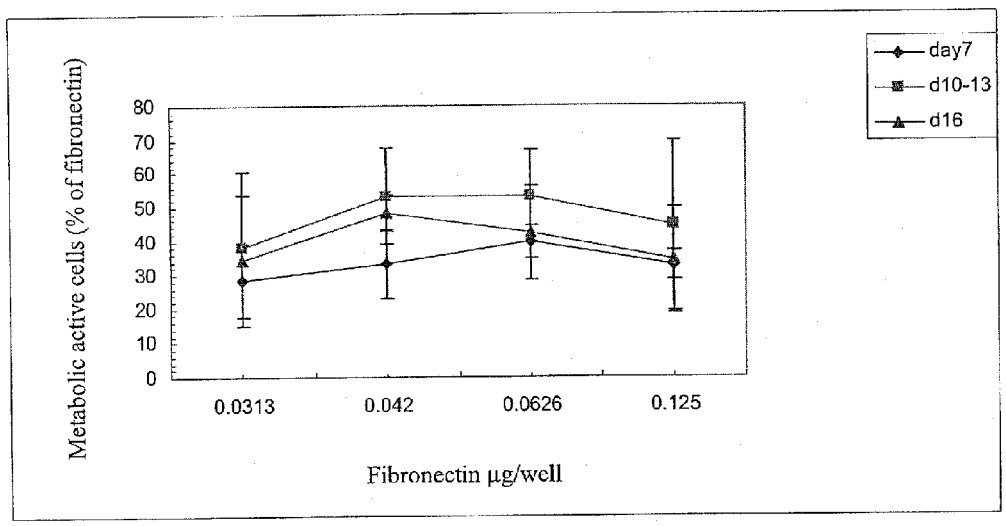

FIG. 5 shows the percentage of metabolic active nucleus pulposus cells on a constant amount of fibronectin and increased amounts of fibrinogen in the coating matrix (A) and on a constant and high amount of fibrinogen and increased amounts of fibronectin in the coating matrix (B). The results in FIG. 5A show that at a constant amount of fibronectin, increasing the amounts of fibrinogen in the coating lead to a decrease in the percentage of nucleus pulposus metabolic active cells. Annulus fibrosus cells were less affected by the fibrinogen addition (results of the annulus fibrosus chondrocytes cultures are not shown). Increased amounts of fibronectin in the presence of a fixed fibrinogen concentration did not improve the percentage of the metabolic active nucleus pulposus cells. Additionally, the results are in line with the previous results which indicate that fibronectin/fibrinogen in a ratio of about 1/5 is more suitable for nucleus pulposus chondrocytes cell attachment as compared to other fibronectin/fibrinogen ratios.

Example 7

Effect of a Three-Dimensional Construct Prepared with Activated VIPCC on the Morphology and Function of Chondrocytes Grown in the Construct Studies (Haudenschild et al. "Differential expression of multiple genes during articular chondrocyte redifferentiation". Anat Rec. 2001; 263:91-98; Li et al. "Chondrocyte phenotype in engineered fibrous matrix is regulated by fiber size". Tissue Eng. 2006; 12:1775-1785; Peretti et al. "A biomechanical analysis of an engineered cell-scaffold implant for cartilage repair". Ann Plast Surg. 2001; 46:533-537) indicate that expansion of chondrocytes in vitro results in phenotype changes, and in a decreased proteoglycan synthesis. The previous examples show that VIPCC having a fibronectin/fibrinogen ratio of about 1/5 is more suitable for growing nucleus pulposus cells. Therefore, the present experiment was aimed to determine the morphology of chondrocyte cells grown in a three-dimensional matrix composed of activated VIPCC. For this purpose, 750 µl of annulus fibrosus or nucleus pulposus cell suspension was prepared using a 5 fold diluted VIPCC, which contains 14 mg/ml clottable fibrinogen. To activate the VIPCC component and form a clot, the above mentioned suspension was placed simultaneously with an equivalent volume of thrombin solution (2 IU, Omrix biopharmaceuticals LTD, IL) in a 6-well plate culture dish. A three-dimensional chondrocyte construct, which contained $6\times10^5$ cells per well was formed.

After formation of the clot the cell-construct was supplemented with 0.5 ml DMEM/Ham's F12 medium containing the above mentioned antibiotics and 10% FBS. The well plate was cultured at 37° C. in a humidified atmosphere of 5% $CO_2$. After 12 hours, the medium was removed and some of the constructs were detached from the side wall using a scalpel in order to decrease tension conditions. Attached constructs, which were considered as grown under condition of higher tension, served as the control group. The constructs were grown in DMEM/Ham's F12 medium containing the above mentioned antibiotics and 10% FBS and incubated for additional 8 or 14 days, for annulus fibrosus or nucleus pulposus, respectively. The medium was discarded and the cultures were fixed with 3.7% paraformaldehyde solution for 10 min, and stained with Alcian blue (Sigma; cat No A5268) for 10 min at room temperature. Alcian blue staining is designed to show Mucopolysaccharides or Glycosaminoglycans (GAGs) characteristically produced by chondrocytes. Chondroitin sulfate, which belongs to the GAGs family, is usually found in the form of proteoglycans which comprises the ground substance in the extra cellular matrix of cartilage tissue.

Figure 6:
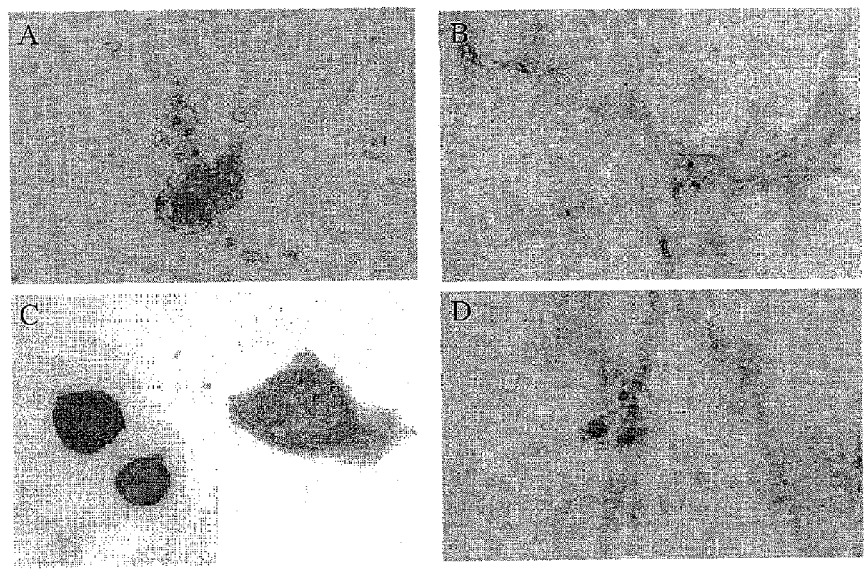
FIGS. 6A-6D: show the morphology and function of annulus fibrosus (upper panel) and nucleus pulposus chondrocytes (bottom panel) in attached (A,C) and detached (B,D) three-dimensional scaffold prepared with VIPCC.

The results are summarized in FIG. 6 and show Alcian blue staining on both annulus fibrosus (FIG. 6, upper panel) and nucleus pulposus chondrocytes (FIG. 6, lower panel). The results demonstrate that both annulus fibrosus and nucleus pulposus chondrocytes are functional and able to manufacture chondroitin sulfate. The detached scaffolds (FIGS. 6B and D) exhibit filamentous and branched-like phenotype whereas attached and more tensed scaffolds (FIGS. 6A and C) assumed a sphere-like phenotype. Thus, the results demonstrate that chondrocytes grown in a three-dimensional scaffold of activated VIPCC are functional and that the tension of the formed scaffold influences the phenotypic differentiation.

Example 8

Figure 7:
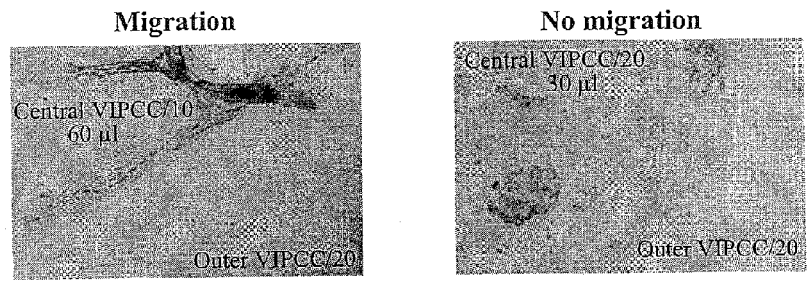
FIG. 7: shows migration of nucleus pulposus cells in activated VIPCC.

The Effect of Different Three-Dimensional Formulations Prepared with Activated VIPCC on the Chondro-Conductive Capability of the VIPCC The objective of the present experiment was to investigate the effect of the formulation on the chondro-conductive characteristic of the VIPCC. Isolated nucleus pulposus chondrocytes suspension was prepared using three solutions of diluted VIPCC (1:2.5, 1:5, 1:10, which contained a final concentration of 28, 14 and 7 mg/ml clottable fibrinogen, respectively) in DMEM/Ham's F12 medium containing the above mentioned antibiotics. Afterwards, the above mentioned suspensions were mixed with an equivalent volume of thrombin component (1 IU/ml, described in U.S. Pat. No. 6,121,232). The final volume of the constructs were 30, 60 or 90 µl with a final VIPCC dilution of 1:5, 1:10 or 1:20 and of 0.5 IU/ml thrombin. All dilutions contained $1.6 \times 10^5$ nucleus pulposus cells. Each mixture was placed in the center of a well of a 24-well plate culture dish. After a clot was formed, 200 µl of a mixture comprised of 0.5 thrombin IU/ml and 20 fold diluted VIPCC, was added at the circumference. After formation of the clot (about 30 min), 0.5 ml growth medium (DMEM/Ham's F12 medium supplemented with antibiotics and 10% FBS) was added and the plate was incubated at 37° C. in a humidified atmosphere of 5% $CO_2$ for 22 days. The chondro-conductive characteristic of the VIPCC was assessed by evaluating the ability of nucleus pulposus chondrocytes to transmigrate from the central construct [(comprised of different dilutions of VIPCC and different volumes (30, 60 or 90 µl] to the peripheral scaffold of VIPCC. After 22 days of culture the medium was discarded and the cultures were fixed with 3.7% paraformaldehyde solution for 10 min, and stained with Alcian blue for 10 min at room temperature. By monitoring the localization of the cells in the plate it was found that transmigration occurred exclusively in the 60 µl volumes of 10 fold diluted activated VIPCC (which contains 7 mg/ml clottable fibrinogen). FIG. 7 shows transmigration of nucleus pulposus chondrocytes as viewed under the microscope with a magnification of X100 in the 60 µl volume of 10 fold diluted activated VIPCC (left panel; the cells aligned and formed a belt-like structure) as compared to nucleus pulposus chondrocytes in the 30 µl volume of 20 fold diluted activated VIPCC that were unable to transmigrate (right). Additionally, chondrocytes in all the experimental groups were able to proliferate in the central construct and were capable of producing chondroitin sulfate (results not shown). These results show that nucleus pulposus chondrocytes sense a chemotactic gradient and transmigration occurs only in the presence of a chemical gradient.

Example 9

Biocompatibility of the VIPCC in Intervertebral Disc Injection

The previous example shows that VIPCC is suitable for use with nucleus pulposus cells. Thus, VIPCC can be used for growing nucleus pulposus cells ex-vivo or can be injected into the intervertebral disc space to promote growth of nucleus pulposus cells in vivo. The following experiment was designed to investigate the biocompatibility of Omrix commercial activated-VIPCC injected into the intervertebral disc space. For this purpose, VIPCC and thrombin were injected into the intervertebral disc of a pig.

Female swine (n=1) weighing 74 kg and at the age of 6 months was housed in an authorized facility according to the current ethical requirements. Anesthesia was induced with an intramuscular mixture of ketamin (10 mg/kg) and xylazine (2 mg/kg).

Physical examination was preformed prior to the surgical procedure (body weight, temperature, heart and respiratory rates). ECG, pulse, and blood pressure were monitored during the procedure.

Surgical procedure: The animal was positioned laterally and bended forward. A contrast agent was used and served as a visual guidance to locate the IVDs cavity using fluorography. The contrast agent used was iodine (0.37 g/ml iodine; Tel Hashomer, Ill.). The injections were preformed using a syringe connected to 23G spinal needle 90 mm ("phoenix" Kobayashi Shoji K.K Tokyo, Japan).

In order to practice the injection procedure, IVDs thoracic vertebrates 10-11 ($T_{10}$-$T_{17}$) were filled with diluted iodine (1:1 with saline).

Once the injection procedure was satisfactory, the sequence of IVD injections was as follows:
1. IVDs $L_1$-$L_2$ and $L_3$-$L_4$ were injected with ~200-300 µl saline.
2. IVDs $L_2$-$L_3$ and $L_4$-$L_5$ were injected with VIPCC and thrombin (described in U.S. Pat. No. 7,125,569) applied simultaneously (similar quantity in the total volume of ~200-300 µl) using Omrix injection device to form a solid gel.

Prior to each injection, a very small amount (present at the tip of the needle) of 1:10 diluted contrasting agent was injected into the IVD space in order to verify the exact application site (a small amount was injected so that enough intradiscal space was left for activated-VIPCC injection).

Figure 8:
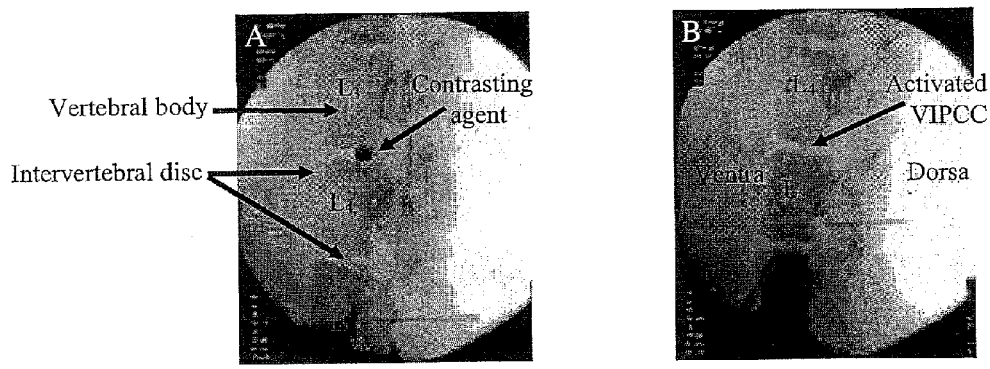
FIG. 8: shows a fluorography image of control (A; saline) and activated-VIPCC (B; prepared with VIPCC and thrombin) injections into the intervertebral disc.

FIG. 8 shows a fluorography image of control (A; saline) and activated-VIPCC (B) injected intervertebral discs. The contrast agent turned invisible in the activated-VIPCC injected IVD.

Photographs and digital video recordings were taken after the injection procedure.

Post-operative care: The animal received non-steroidal analgesics (30 mg/kg dipyron) and antibiotics (0.02 ml/kg marbocyl) for the first 2 days post operation. The animal was hospitalized for 14 days and an observation of ambulatory activities (e.g. standing, walking), drinking and eating patterns and behavior characteristics were monitored.

During the observation period the animals drank and ate normally. In the first six days, the animal's ability to wake up was improved. The animal showed weakness of the rear legs and crossed her legs while walking. By the sixth day, the animal was able to walk steadily. No fever was detected during the observation period. On day 13 the animal's weight was 77.5 kg (gained 4.5 kg).

Sample collection: The animal was sacrificed 14 days after surgery and the lumbar spine was removed for histological analysis.

Figure 9:
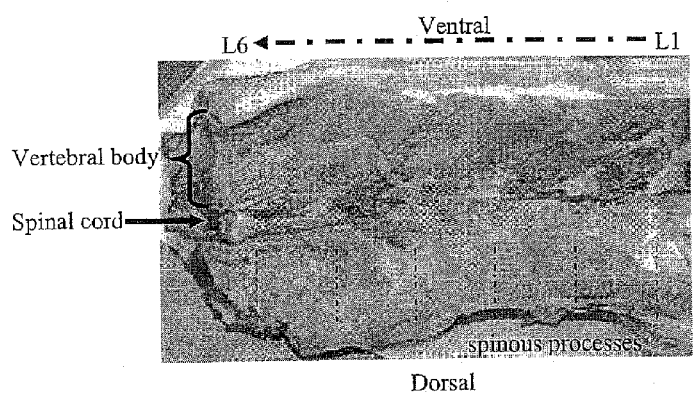
FIG. 9: shows the isolated lumber spine 14 days after the injection procedure described in FIG. 8.

The injected isolated lumber spine showed no sign of damage or inflammation to the surrounding tissue (FIG. 9).

The injected IVDs specimens were isolated, according to the above procedure (Example 1), and decalcified in 8% formic acid until the tissue was soft enough for histological assessment.

Figure 10:
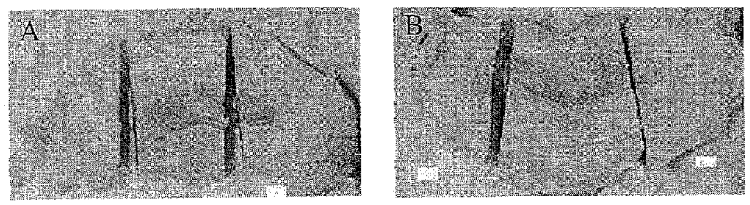
FIG. 10: shows decalcified intervertebral discs (IVDs) of saline (A) and activated-VIPCC (B) injections as described in FIG. 8.
Figure 11:
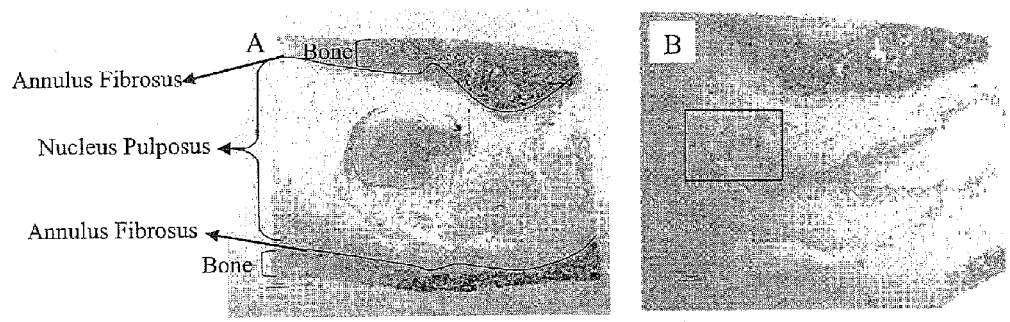
FIG. 11: shows histological studies of the nucleus pulposus region of saline (A) and activated-VIPCC (B) IVDs injections described in FIG. 8.
Figure 12:
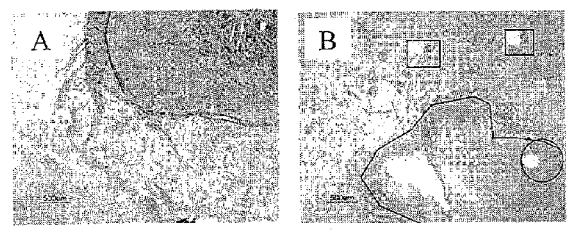
FIG. 12: shows the central region of the nucleus pulposus of control (A) and activated-VIPCC (B) IVDs injections described in FIG. 8.
Figure 13:
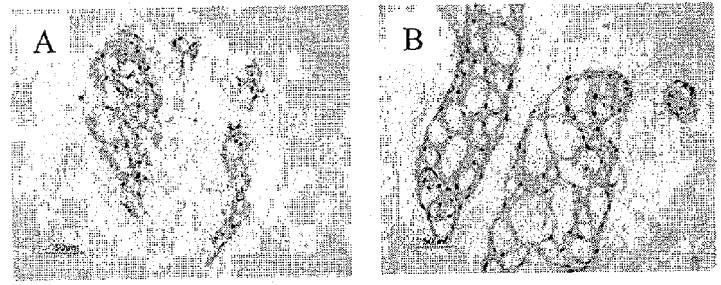
FIG. 13: shows clusters of nucleus pulposus in the peripheral region of control (A) and activated-VIPCC (B) IVDs injections.

FIG. 10 shows control saline injected (A) and activated-VIPCC injected (B) decalcified IVDs specimens. Histological assessments were done by Hematoxylin and Eosin staining of the nucleus pulposus region. Control saline injected IVDs showed clusters of chondrocytes with a typical necrotic damage, pyknotic nuclei and karyolysis (FIGS. 11A, 13A). Activated-VIPCC injected IVDs showed groups of viable chondrocytes in the peripheral region with a typically vacuolated cytoplasm structure (FIGS. 11B, 13B). The central region of the nucleus pulposus showed an intense coloring compared to the peripheral region in both experimental groups (FIG. 12A-*control* and B-activated-VIPCC injections). In the control group the differences were more pronounced. The low intensity color in the peripheral region indicates a normal structure with scattered cellular clusters, whereas the intensed color presents necrotic cells. The above shown results indicate that injection with activated-VIPCC does not result in any structural changes and preserves the typical structure of chondrocyte tissue.

Example 10

Effect of a Three-Dimensional Scaffold Prepared with Activated VIPCC on the Morphology and Function of Nucleus Pulposus Chondrocytes in an Ex-Vivo IVD Organ Culture The objective of the experiment was to determine the morphology and functionality of nucleus pulposus chondrocytes when disposed in Omrix commercial activated-VIPCC construct within an isolated IVD.

Two pig lumbar spines (L1-L6) were used in this experiment, one for harvesting cells and the other for obtaining separated IVDs lacking nucleus pulposus tissue.

The first spine was sterilized as described in Example 1 and the vertebral bodies were dissected in the middle so that isolated intervertebral discs could be obtained. Then, the cells were harvested as follows: 250 µl digestion solution containing 6 mg/ml collagenase and 2 mg/ml hyaluronidase in PBS (Sigma cat No C-6885 and H-2126, respectively) was injected into the nucleus pulposus tissue using a 1 ml syringe connected to 16G needle. The intravertebral discs containing the digestion solution were incubated at 37° for 1 h. Following the incubation period, the digested nucleus pulposus tissue was drawn and viability was evaluated using the Trypan blue dye exclusion method as follows: 80 µl Trypan blue solution (Sigma cat No T8154; 0.15% diluted in PBS) was mixed with 20 µl cell suspension and cell viability was measured using a hemocytometer. Cell viability was defined by the ratio of the viable cell number to the total cell number. In all experiments the viability exceeded 80%.

The second spine was cut in the mid-vertebral bodies with an electric bone saw and the nucleus pulposus tissue was forcefully aspirated (0.2-0.5 ml) through a 16 G needle (without the use of proteolytic enzymes) to get separated IVDs lacking nucleus pulposus tissue. The above mentioned harvested cells (extracted by a digestion solution) were suspended in 20 fold diluted VIPCC (in DMEM/Ham's F12 supplemented with the above mentioned antibiotics) component ($5 \times 10^5$ cells per ml) and injected simultaneously with 1000 IU/ml thrombin solution (equal quantity in the total volume of ~200-500 µl) into the IVDs lacking nucleus pulposus tissue through a 16 G needle attached to an injection device (Omrix, Ill.). After a clot was formed, the injected IVDs were placed on a plastic platform within a plastic box pre-filled with 1 cm PBS containing antibiotics (0.2% Pen-Strep). This way a humid environment was provided (the IVDs had no direct contact with the PBS).

The cell-injected IVDs were incubated at 37° C. for 2, 3 or 6 days. IVDs incubated for 1 hour served as the control group. Following incubation, the discs were cut in halve using a scalpel and the nucleus pulposus area content was removed and fixed with 3.7% formaldehyde solution for at least 24 hours. This step was followed by immersion in PBS (10 minutes×3 times). The samples were dehydrated in an ascending series of alcohols, 70%, 85%, 95% and 3 times with 100% ethanol (20 min each wash) followed by washing in histoclear (Gadot Biochemical Industries Ltd. cat No L80033240) three times for 30 min each. Then, the samples were placed in a 1:1 mixture of histoclear and paraffin and heated in an oven at 60° C. for 1 hour×2. The specimens were then subjected to the following paraffin immersions: 2 h at 60° C., over-night at 60° C. and twice at 60° C. for 2 h. The tissue was then embedded in plastic histology cassettes full with hot paraffin and left to cool at 4° C.

The paraffin-embedded tissues were sectioned serially at 8 µm thickness and stained for chondroitin sulfate using Alcian blue as previously described. For counterstaining nuclear fast red (Sigma cat No 8002) was used according to manufacturer's instructions.

Figure 14:
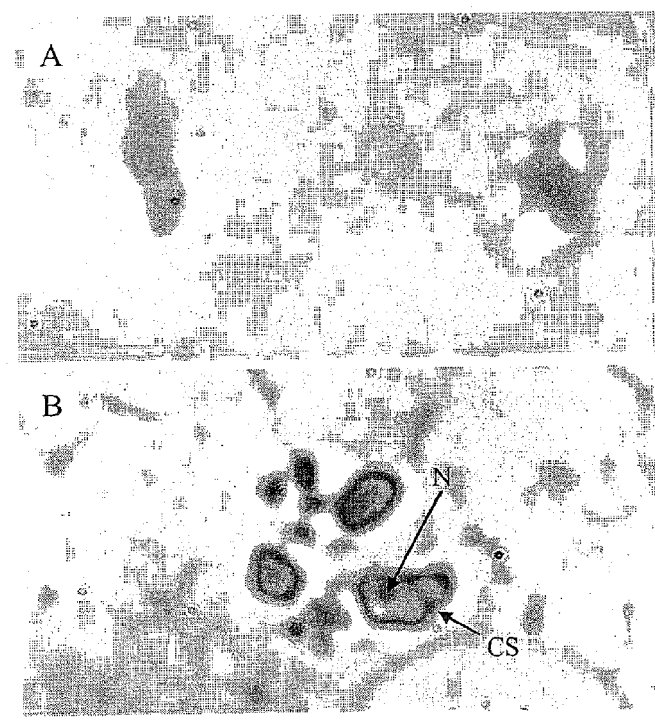
FIG. 14: shows the morphology and chondroitin sulfate production of nucleus pulposus chondrocytes cells disposed in three dimensional scaffolds formed of 20 fold diluted VIPCC and thrombin mixture within isolated intervertebral discs. Histological assessment was done using an inverted fluorescent microscope 1 hour and 3 days (A and B, respectively) following the injection procedure. N—nucleus; CS—chondroitin sulfate. Chondroitin sulfate production is apparent on the cell membrane (arrow).

FIG. 14 shows the morphology of nucleus pulposus cells and chondroitin sulfate production of chondrocytes disposed in three dimensional scaffolds formed of 20 fold diluted VIPCC and thrombin mixture within isolated intervertebral discs. Histological assessment was done using an inverted fluorescent microscope 1 hour, 3 and 6 days following the injection procedure.

The control group exhibited no expression of chondroitin sulfate in the cells surrounding environment (FIG. 14A). Expression of chondroitin sulfate could be seen from the third day onwards. On the third (FIG. 14B) and sixth day (not shown) following the injection a significant expression of chondroitin sulfate is apparent throughout the whole clot and around the cell. On the sixth day a large space was seen in the area which surrounds the cell, apparently as a result of an increase in cell number which leads to secretion of proteolytic enzymes and eventually to lysis of the construct (not shown).

Also, the results demonstrate that chondrocytes cells assumed a typical rounded phenotype in the 3D scaffold formed of activated-VIPCC at all time points following the injection (FIG. 14B).

These results indicate that the activated-VIPCC supports growth and functionality of the nucleus pulposus cell injected within the intervertebral discs, enabling the cells to maintain their sphere like wild type morphology and to produce chondroitin sulfate.

Example 11

Intravertebral Disc Height Restoration Using Injectable Activated-VIPCC

The nucleus pulposus is able to resist compressive loads and the annulus fibrosus withstands tension and gives mechanical strength (Revell et al "Tissue engineered intervertebral disc repair in the pig using injectable polymers". J Mater Sci Mater Med. 2007; 18:303-308). The following example illustrates the ability to use Omrix commercial activated-VIPCC to resist compressive load and substantially retain the original height of the disc. In order to obtain isolated intervertebral discs, pig lumbar vertebral bodies were cut in the middle using an electric bone saw. Afterwards, the isolated intervertebral discs were flattened using an electric sander to produce smooth, parallel symmetrical upper and lower surfaces. The isolated intervertebral discs were placed in a tension and compression testing machines (LF plus, LLOYD instruments Ltd, Hampshire, UK) and compression was measured under gradually increasing loads (25-500 N).

Each intravertebral disc was measured at a load of 10 N in order to determine the initial sample height followed by compression measurements at 25-500 N. Then, the intravertebral discs were emptied by injection of a digestion solution as described in Example 10. Next, two syringes connected to 16 G needles were applied at opposite ends of the isolated IVD and up to 2 ml PBS was injecting into the IVD. The disc space was emptied and filled several times and then the IVD content was discarded. The latter procedure was carried out three times. This procedure was repeated once using about 2 ml EDTA (10 mM; Riedel-de-Haen cat No 34549). Subsequently, the compression of the emptied discs was measured under increasing loads. Compression at 500 N was considered as the maximal compression possible value. The emptied discs were punctured twice using a 16 G needle resulting in a total of 4 16 G holes.

The punctured-emptied discs were injected with PBS or VIPCC and thrombin (applied simultaneously at equivalent volumes; Omrix biopharmaceuticals LTD IL) using Omrix injection device. The solutions were injected into the existing punctures until excess solution was spilt out of the injection site. The re-filled intravertebral discs were incubated at room temperature for about 30 min. Following the incubation period, compression measurements of the filled disc were carried out under the different loads. All measurements were repeated 5 times.

Figure 15:
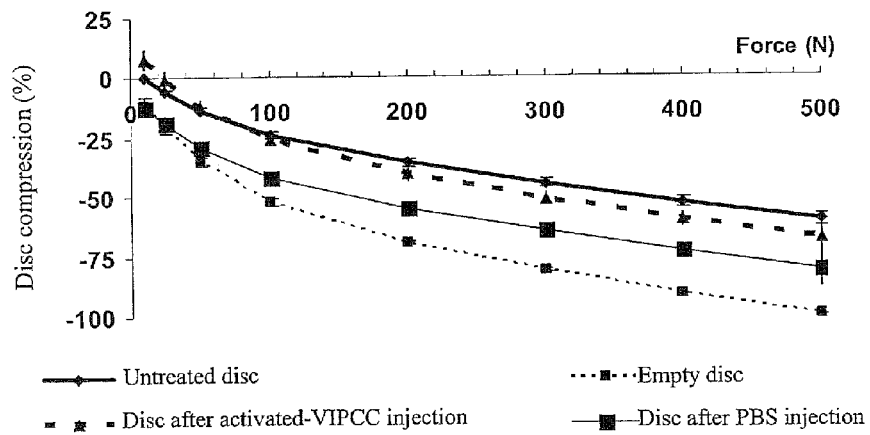
FIG. 15: shows the percent of disc compression under increasing force load of untreated disc, empty disc, and re-filled discs (PBS or VIPCC and thrombin).

FIG. 15 demonstrates the percent of disc compression under increasing force load of untreated disc, empty disc, and re-filled discs (PBS or VIPCC and thrombin). The results are expressed as the delta in compression at a specific load (compression of un-treated disc under 10 N load–compression of re-filled disc under X N load) divide to the maximal compression possible value according to the following formula:

$$\frac{\text{(Compression of un-treated disc under 10 N load)} - \text{(Compression of re-filled disc under } X \text{ N load)}}{\text{(Compression of empty disc under 500 N load)} - \text{(Compression of untreated disc under 10 N load)}} \times 100$$

Figure 16:
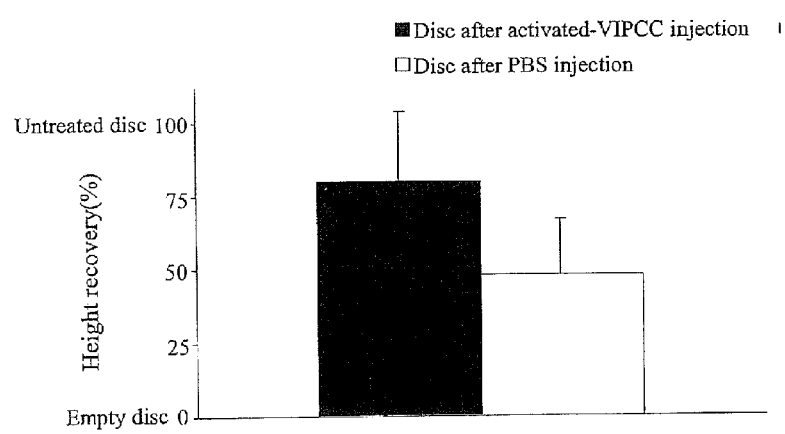
FIG. 16: shows the height recovery of discs injected with either activated VIPCC or PBS. The results are based on the measurements displayed in FIG. 15 (compression under 500 N). The results are presented as percentage of the maximal compression possible of un-treated disc under 500 N load in the same experiment (100%).

FIG. 16 demonstrates the height recovery of discs injected with either activated VIPCC or PBS. The results are based on the measurements displayed in FIG. 15 (compression under 500 N). The results are presented as percentage of the maximal compression possible of un-treated disc under 500 N load in the same experiment (100%) according to the following formula:

$$\frac{\text{(Compression of un-treated disc under 500 N load)} - \text{(Compression of re-filled disc under 500 N load)}}{\text{(Compression of untreated disc under 500 N load)} - \text{(Compression of emptied disc under 500 N load)}} \times 100$$

disc lead to an increase in disc compression. The compression behavior of activated-VIPCC injected discs as a function of increased force is similar as the untreated discs.

The results also show that activated-VIPCC injected discs recovered their initial height as compared to PBS injected discs.

This clearly shows that activated-VIPCC can function to preserve the normal disc height and is able to resist compressive loads as natural nucleus pulposus.

The invention claimed is:

1. A method for treating a spine disease, disorder or condition comprising administering to a subject in need viral inactivated-plasma cryoprecipitate concentrate (VIPCC) in combination with notochordal-derived cells, wherein the VIPCC has an initial fibronectin/fibrinogen relative concentration of about 1/10 to about 1/5, with the proviso that tranexamic acid and bovine aprotinin are absent from the cryoprecipitate concentrate.

2. A method for treating a spine disease, disorder or condition selected from the group consisting of disc herniation, fissured disc, spinal stenosis, black disc, disc pain, central nervous system defect selected from a dura defect, brain and spinal cord injuries due to neurosurgery, trauma, ischemia, hypoxia, neurodegenerative disease, metabolic disorder, infectious disease, compression of the intervertebral disc, tumors and/or autoimmune disease comprising administration of viral inactivated-plasma activated cryoprecipitate concentrate in combination with notochordal-derived cells, wherein prior to activation said cryoprecipitate comprises an initial fibronectin/fibrinogen relative concentration of about 1/10 to about 1/5 and the cells, with the proviso that bovine aprotinin is absent from the cryoprecipitate concentrate.

3. The method according to claim 2, for treating an intervertebral disc disease, disorder or condition.

4. A method for restoring the intervertebral disc height comprising administering a viral inactivated-plasma activated cryoprecipitate concentrate in combination with notochordal-derived cells, wherein prior to activation said cryoprecipitate comprises an initial fibronectin/fibrinogen relative concentration of about 1/10 to about 1/5 and the cells, with the proviso that tranexamic acid and bovine aprotinin are absent from the cryoprecipitate concentrate.

5. The method according to claim 1, wherein the VIPCC comprises a contrast agent.

6. The method according to claim 5, wherein the contrast agent is iodine.

7. The method according to claim 1, for restoring the intervertebral disc height.

8. The method according to claim 1, for preventing intervertebral disc herniation.

9. The method according to claim 1, wherein the disease is an early stage of intervertebral degenerative disease.

10. The method according to claim 1, wherein the VIPCC is activated and the activated VIPCC serves as a scaffold for reconstruction of injured or ruptured spinal cord.

11. The method according to claim 1, for treating an intervertebral disc disease, disorder or condition.

* * * * *